(12) United States Patent
Yoon

(10) Patent No.: US 6,270,484 B1
(45) Date of Patent: *Aug. 7, 2001

(54) SAFETY PENETRATING INSTRUMENT WITH EXPANDIBLE PORTION AND METHOD OF PENETRATING ANATOMICAL CAVITY

(76) Inventor: InBae Yoon, 2101 Highland Ridge Dr., Phoenix, MD (US) 21131

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/251,470

(22) Filed: Feb. 17, 1999

(51) Int. Cl.$^7$ .................................................. A61M 25/00
(52) U.S. Cl. ............................................................ 604/264
(58) Field of Search .................................. 604/264, 162, 604/164.04, 164.03, 164.06, 174–175, 178–180, 506, 192, 263

(56) References Cited

U.S. PATENT DOCUMENTS

| | | |
|---|---|---|
| 3,978,863 | 9/1976 | Fettel et al. . |
| 4,020,831 | 5/1977 | Adler . |
| 4,073,288 | 2/1978 | Chapman . |
| 4,531,943 | 7/1985 | Van Tassel et al. . |
| 4,838,280 * | 6/1989 | Haaga ..................................... 128/751 |
| 4,895,559 | 1/1990 | Shippert . |
| 5,069,669 | 12/1991 | Kole . |
| 5,176,648 * | 1/1993 | Holmes et al. ........................ 604/164 |
| 5,304,148 | 4/1994 | Lannoye et al. . |
| 5,370,625 * | 12/1994 | Shichman .............................. 604/174 |
| 5,401,247 * | 3/1995 | Yoon ..................................... 604/165 |
| 5,423,760 | 6/1995 | Yoon . |
| 5,423,770 | 6/1995 | Yoon . |
| 5,484,426 * | 1/1996 | Yoon ..................................... 604/286 |
| 5,556,412 | 9/1996 | Hill . |
| 5,637,097 | 6/1997 | Yoon . |
| 5,707,359 | 1/1998 | Bufalini . |
| 5,713,869 | 2/1998 | Morejon . |
| 5,882,340 | 3/1999 | Yoon . |
| 5,882,345 * | 3/1999 | Yoon ..................................... 604/264 |
| 5,997,524 * | 12/1999 | Burbank et al. ....................... 604/506 |

* cited by examiner

Primary Examiner—Sharon Kennedy
Assistant Examiner—Ann Y Lam
(74) Attorney, Agent, or Firm—Blank Rome Comisky & McCauley LLP

(57) ABSTRACT

A safety penetrating instrument for penetrating an anatomical wall or a body lumen comprises an elongated penetrating member having proximal and distal ends. The distal end of the elongated penetrating member has a sharp or blunt tip for piercing the anatomical wall or penetrating the body lumen. A covering for the tip comprises an expandible sponge material having a first state with a first hardness and a second state with a second hardness less than the first hardness. Hydrating the covering material causes it to transition from the first hardness state to the second hardness state so that when the distal end of the elongated penetrating member passes from a position outside the anatomical wall or body lumen to a position inside the anatomical wall or lumen, the covering transitions from the first state to the second state to form a relatively soft protective member for the sharp or blunt tip. A method of safety penetration comprises the steps of covering the tip with an expandible sponge material and hydrating the covering during penetration of the anatomical wall or body lumen. The safety penetrating instrument may comprise a trocar with a portal sleeve, a cannula, needle, catheter or the like and may be provided with devices for optical viewing, imaging and/or sensing parameters, such as pressure, temperature, pH and other chemistry.

24 Claims, 17 Drawing Sheets

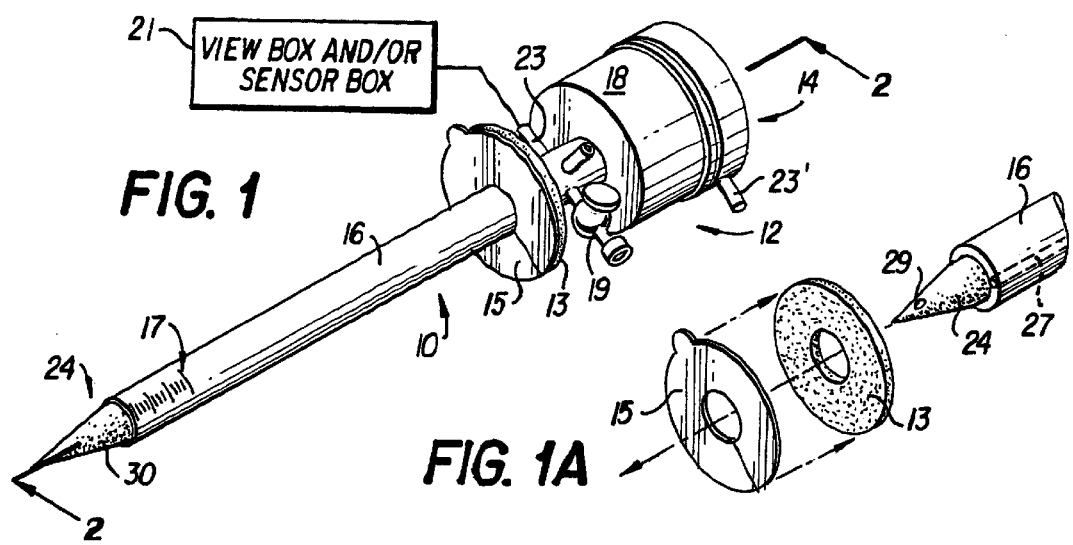
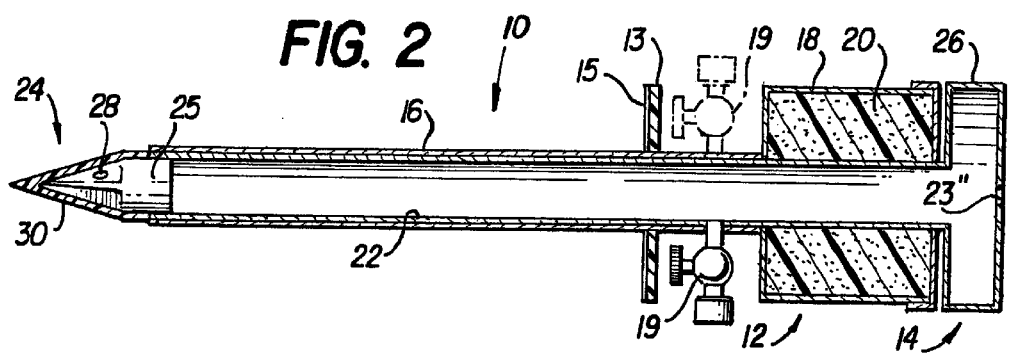
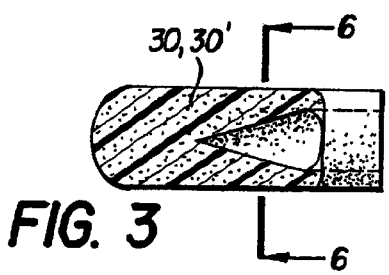 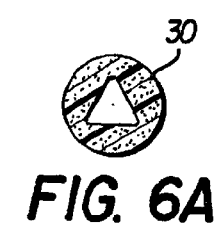 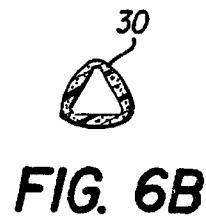
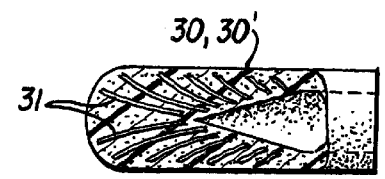 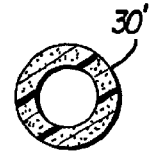 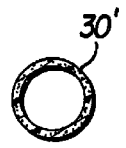

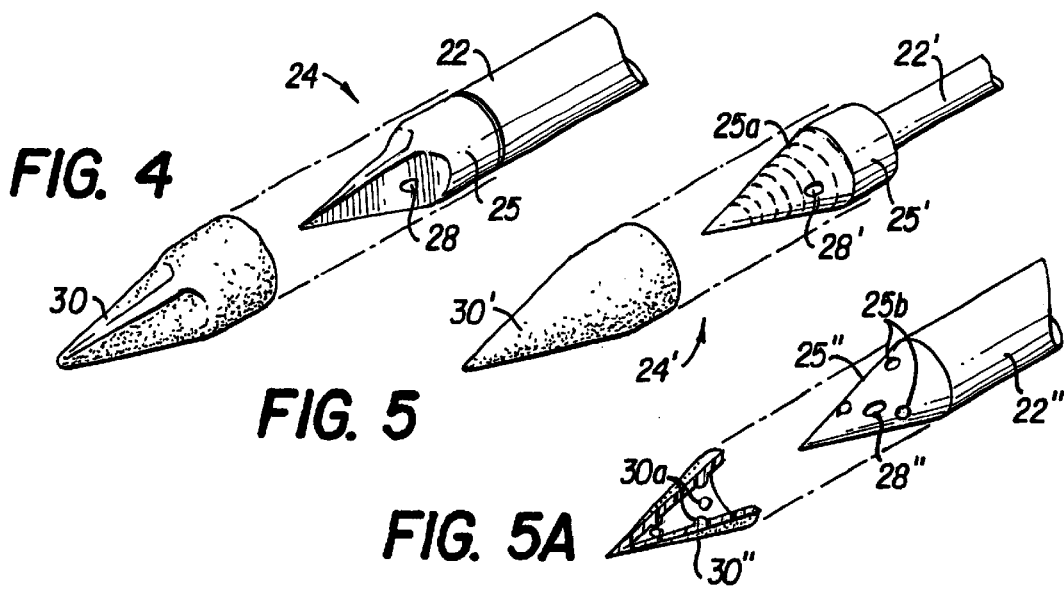
FIG. 4
FIG. 5
FIG. 5A
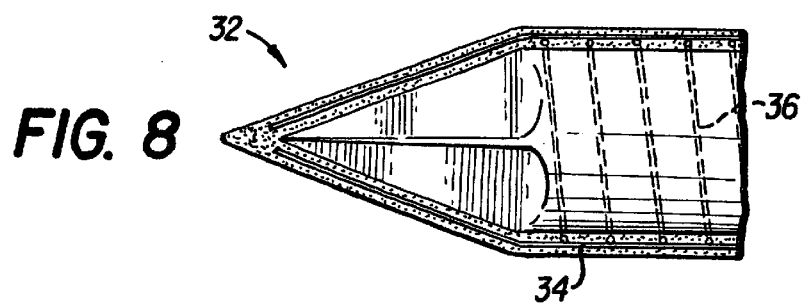
FIG. 8
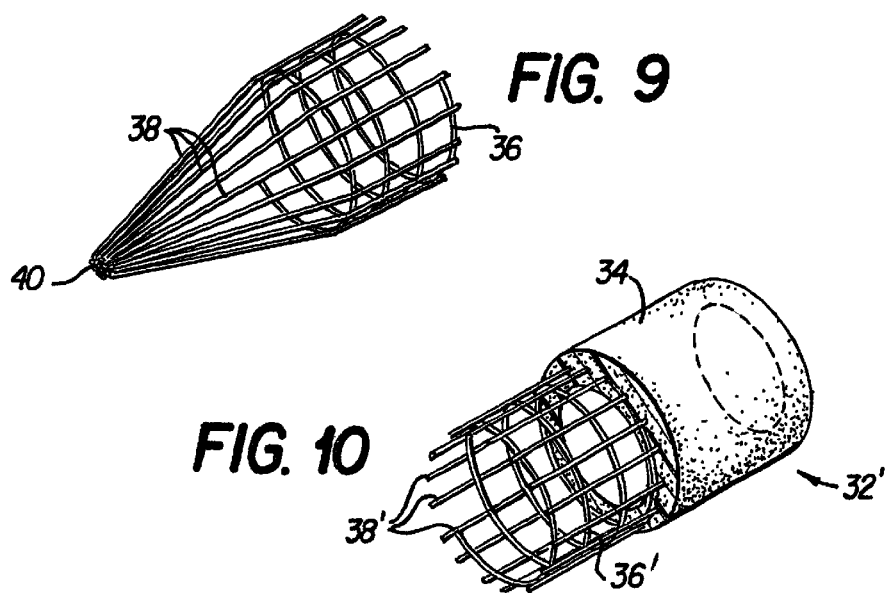
FIG. 9
FIG. 10

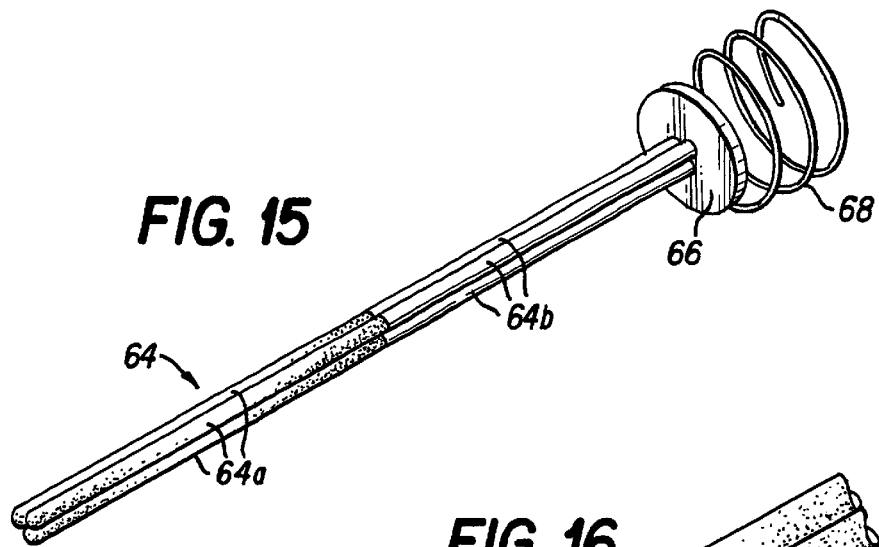
FIG. 15
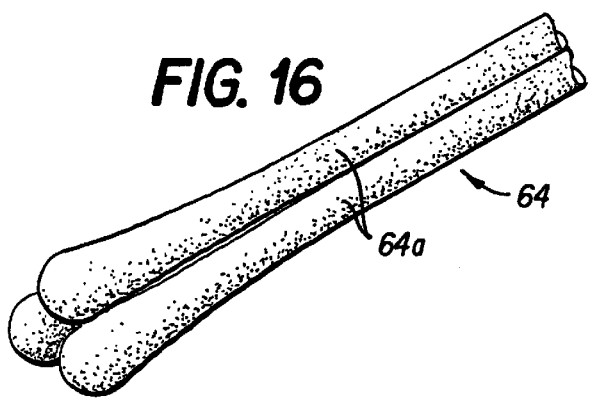
FIG. 16
FIG. 17
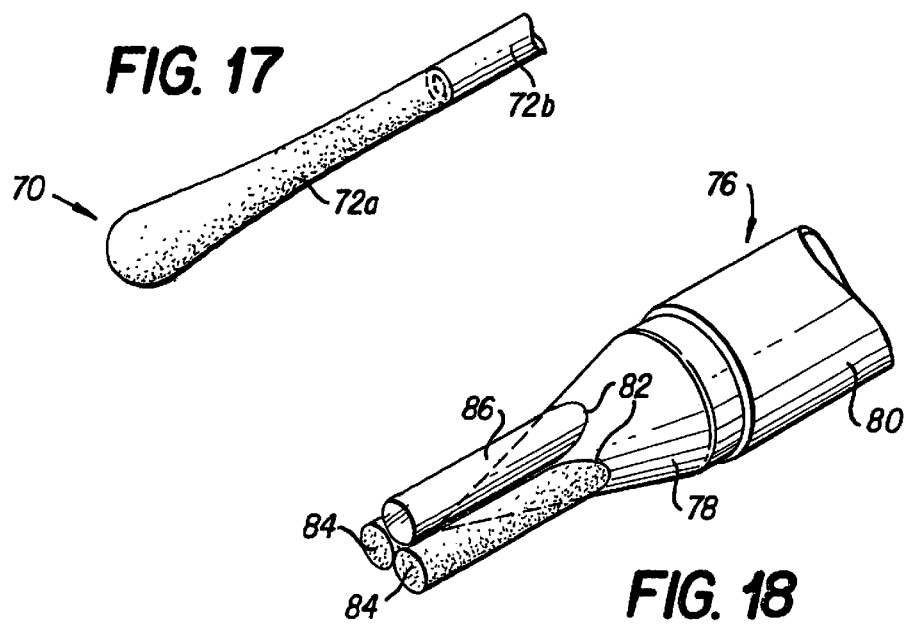
FIG. 18

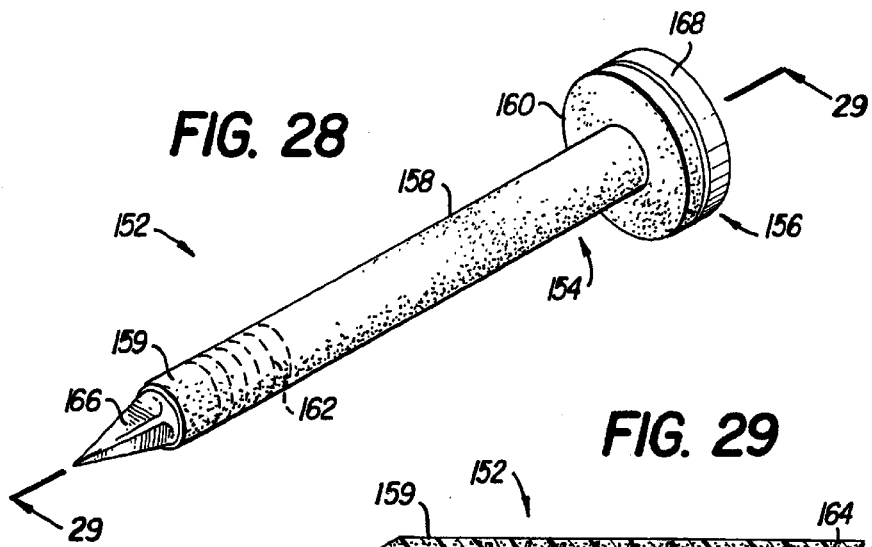
FIG. 28
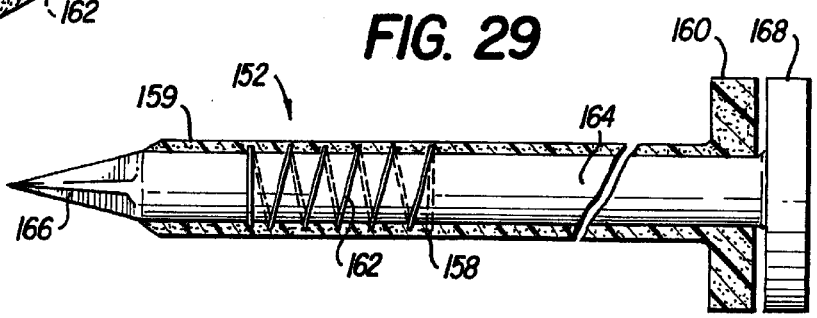
FIG. 29
 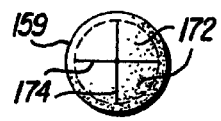  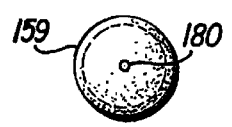
FIG. 30A  FIG. 30B  FIG. 30C  FIG. 30D
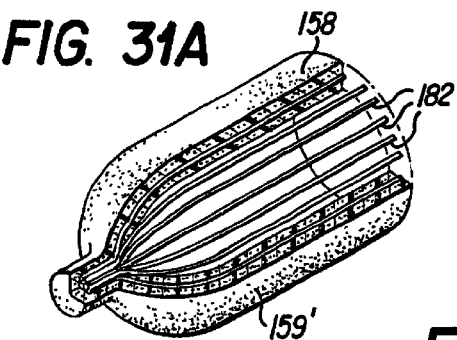 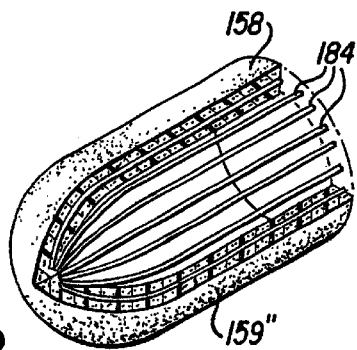
FIG. 31A  FIG. 31B

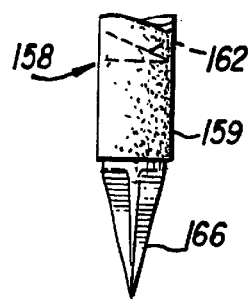
FIG. 33A
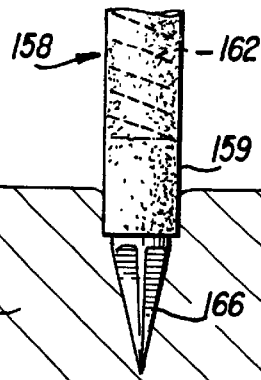
FIG. 33B
FIG. 33C
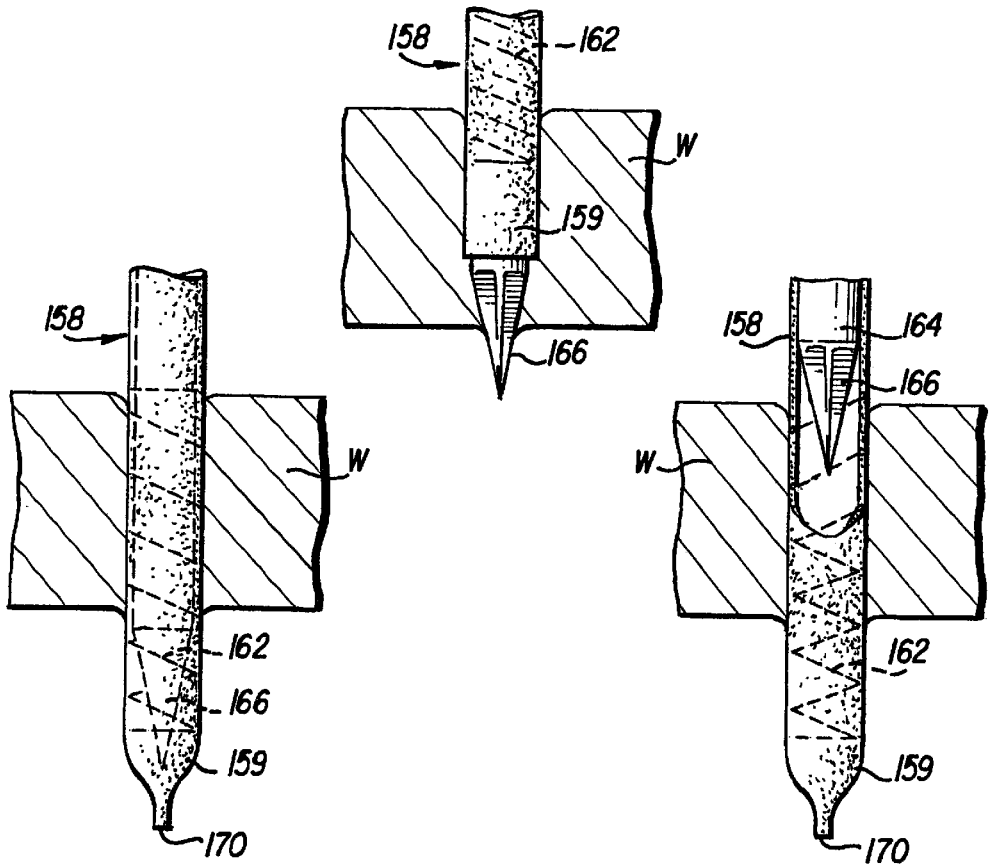
FIG. 33D  FIG. 33E

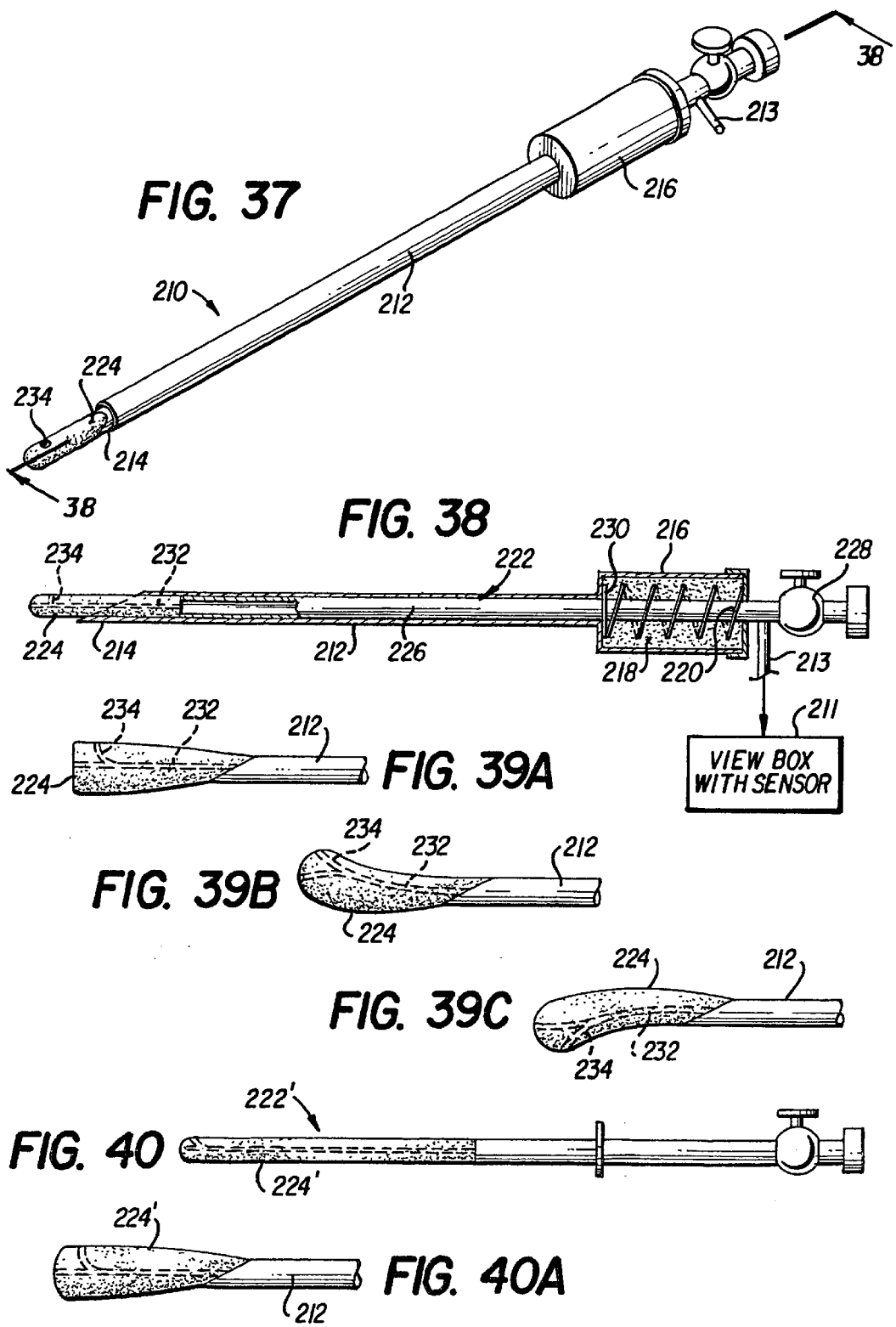

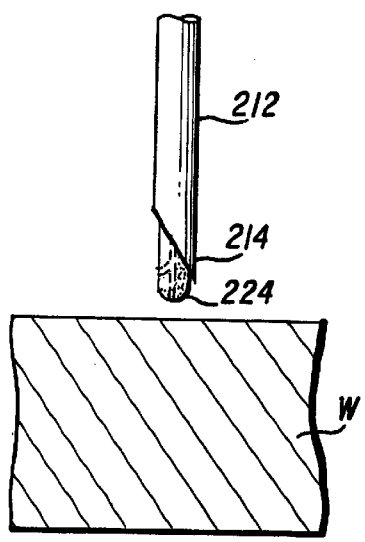
FIG. 41A
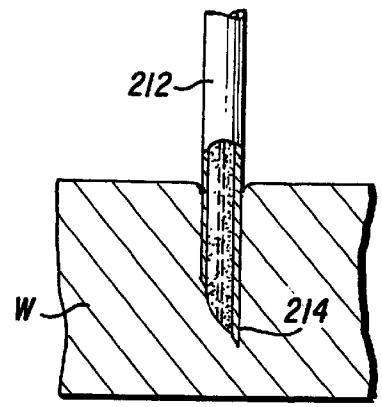
FIG. 41B
FIG. 41C
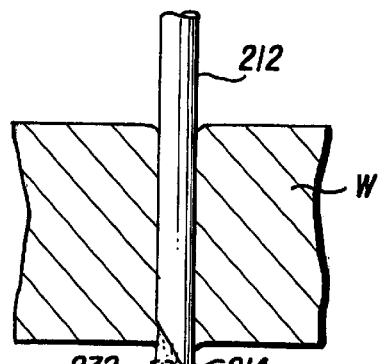
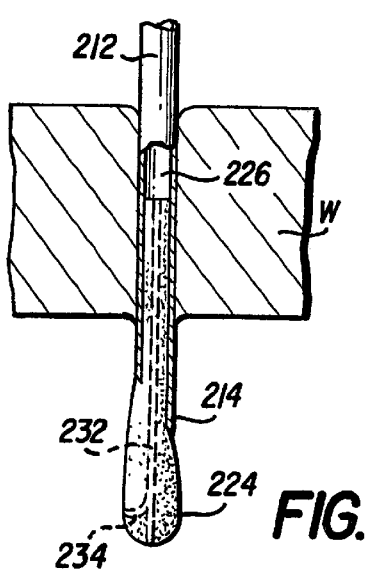
FIG. 41D
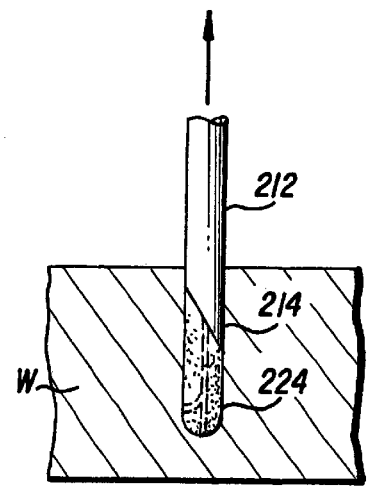
FIG. 41E

SAFETY PENETRATING INSTRUMENT WITH EXPANDIBLE PORTION AND METHOD OF PENETRATING ANATOMICAL CAVITY

BACKGROUND OF THE INVENTION

1. Field of the Invention

The present invention relates to safety penetrating instruments for minimally invasive surgical and diagnostic procedures and other procedures in which an anatomical cavity must be penetrated. More particularly, the present invention relates to safety penetrating instruments for use in forming portals for establishing communication with anatomical cavities and body lumens wherein tissue and organ structures are protected from the tips of the penetrating members and to methods of penetrating anatomical cavity walls and body lumens with safety penetrating instruments.

2. Description of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for a number of procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the cavity wall is penetrated, the lack of tissue resistance can result in the sharp tip traveling too far into the cavity and injuring adjacent tissue or organ structures. Accordingly, once penetration is achieved, it is desirable to protect the tissue or organ structures in or forming the cavity from inadvertent contact with or injury from the sharp tip of the penetrating member.

Various safety penetrating instruments have been proposed, generally falling into protruding and retracting categories, or combinations of protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe. In safety penetrating instruments that combine elements of the protruding and retracting instruments, typically, the penetrating member of the safety penetrating instrument is retracted and one or more safety members are extended to protrude distally beyond the distal end of the penetrating member. Safety penetrating instruments of the forgoing types are disclosed, for example, in my prior U.S. Pat. Nos. 5,807,402; 5,645,557; 5,645,556; 5,607,439; 5,591,189; 5,584,848; 5,575,804; 5,573,545; 5,571,134; 5,569,289; 5,827,315; 5,810,866; 5,730,755; 5,713,870; 5,707,362; 5,688,286; 5,676,683; 5,676,156; 5,676,682; 5,676,681; 5,665,102; 5,645,076; 5,634,934; 5,681,271; 5,607,396; 5,591,193; 5,191,190; 5,586,991; 5,584,849; 5,573,511; 5,569,288; 5,569,293; 5, 549,564; 5,536,256; 5,478,317; 5,466,224; 5,445,617; 5,431,635; 5,423,770; 5,423,760; 5,401,247; 5,360,405; 5,350,393; 5,336,176; 5,330,432; 5,226,426.

While the protruding, retracting and combination protruding/retracting safety penetrating instruments disclosed in my aforementioned patents have been generally well received, there is still a need in the art for a safety penetrating instrument that is not limited by the disadvantages inherent in such protruding, retracting and protruding/retracting safety penetrating instruments. In protruding instruments, the force required to penetrate the cavity wall necessarily includes the force required to overcome the spring bias on the safety member as well as the resistance of the cavity wall. Insuring that the safety member protrudes after penetration normally requires increasing the spring bias on the safety member and, consequently, the force to penetrate the cavity wall. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

Another type of safety penetrating instrument is disclosed in my copending U.S. Pat. No. 5,882,345 filed May 22, 1996, the disclosure of which is incorporated herein by reference. One form of the penetrating member disclosed in that application is made of an absorbent material which, in its dry state, is sufficiently hard to penetrate an anatomical cavity and in its wet or hydrated state becomes soft and pliant so as to avoid injury to internal organs and other tissue in the cavity. While this type of safety penetrating instrument is acceptable in some endoscopic procedures, the possibility of premature hydration and softening of the absorbent material during penetration of the instrument by reason of contact with body fluids limits the effectiveness of this design in many procedures.

It would be desirable, therefore, to provide a safety penetrating instrument that is not limited by the disadvantages of the foregoing types of safety penetrating instruments, but rather provides the necessary protection of tissue and organs by means of a unique, in situ safety shield or sleeve structure.

SUMMARY OF THE INVENTION

Accordingly, it is a primary object of the present invention to overcome the disadvantages of the prior art protruding, retracting and protruding/retracting safety penetrating instruments by providing a safety penetrating instrument having a sharp, rigid penetrating member that is gradually converted from a penetrating state or condition into a safety state or condition during the time as the penetrating member passes through the tissue forming the anatomical cavity wall.

It is another object of the present invention to provide a safety penetrating instrument with an in situ protecting safety structure for the penetrating member that requires no protruding or retracting members for penetration of the instrument into an anatomical cavity.

Yet another object of the present invention is to utilize an in situ expandable safety element or a protruding, expandable probe as a safety member in a safety penetrating instrument wherein the safety element or probe expands in response to absorption of liquid during penetration of the penetrating member through the wall of an anatomical cavity to provide a soft compliant covering for the penetrating member.

Still another object of the present invention is to utilize an expandible sponge as a safety sleeve member to gradually expand and surround a sharp, rigid penetrating member during its penetration of the anatomical cavity wall so that when the rigid penetrating member has passed through the cavity wall it is completely enclosed in a protective expanded sponge.

A further object of the present invention is to utilize an expandible sponge as a coating on a sharp, rigid penetrating member which gradually expands and surrounds the rigid penetrating member during its penetration of the anatomical cavity wall so that when the rigid penetrating member has passed through the cavity wall it is completely enclosed in the expanded sponge coating.

Yet another object of the invention is to provide a safety penetrating instrument for flexible and rigid blunt tipped members, such as catheters and the like, to improve the comfort and safety of such instruments.

Some of the more important advantages of the present invention over the prior art safety penetrating instruments are the simplicity of design and construction of the safety penetrating instrument which advantageously has fewer moving parts than the prior protruding and retracting instruments. The safety member or structure of the present invention is an expandible sponge, such as, for example, a polyvinyl alcohol sponge, that in some embodiments is applied to the penetrating member in the form of a hard, dry coating or as a hard, dry sleeve slidable onto the penetrating member and which, when hydrated during passage through the wall of an anatomical cavity, becomes soft and compliant. In other embodiments, the safety member or structure is constructed as one or more expandible sponge probes retracted into a sharp, rigid penetrating member in a dry or hardened state and which are hydrated during passage through the wall of an anatomical cavity, and after passage through the wall are extended under spring bias forwardly from the rigid penetrating member in a soft and compliant state to cover or surround the sharp, rigid penetrating member.

The safety members for the penetrating member of the safety penetrating instrument of the present invention can be inexpensively manufactured and may be disposable so that they can be discarded after each use. This results in a safety penetrating instrument with a minimum number of components to reduce cost, and allows economical, single-patient use. It is also contemplated according to the invention that the safety penetrating instrument of the present invention can be refurbished after each use by replacement of the expandible sponge safety member whether that member is in the form of a coating, a sleeve or a probe.

The preferred embodiment of the present invention is generally characterized as a safety penetrating instrument having a cannula, a sharp, rigid penetrating member disposed within the cannula, and a safety member, such as an expandible sponge sleeve, covering or coating for the sharp, rigid penetrating member or one or more probes made of an expandible sponge material extending from the sharp, rigid penetrating member. The expandible sponge material may be a polyvinyl alcohol sponge or other type of expandible sponge or foam that has sufficient hardness in its dry state to maintain its stiffness during penetration of the wall of an anatomical cavity.

Another embodiment of the present invention is characterized as a safety penetrating instrument that penetrates the body by way of a body lumen, such as the urethra. The instrument may be in the form of a flexible or rigid catheter, such as a Foley catheter, cardiac catheter or the like, with a safety member, such as an expandible sponge plug, sleeve, covering or coating for the penetrating tip of the catheter A further aspect of the present invention is generally characterized in a method of forming a portal in a wall of an anatomical cavity including the steps of penetrating the anatomical cavity wall with a penetrating member of a safety penetrating instrument having a protective state where the penetrating member is covered with an expandible sponge material coating or sleeve that expands when hydrated by a liquid, including body fluids.

With the foregoing and other advantages and features of the invention that will become hereinafter apparent, the nature of the invention may be more clearly understood by reference to the following detailed description of the invention, the appended claims and the several views illustrated in the drawings.

BRIEF DESCRIPTION OF THE DRAWINGS

FIG. 1 is a perspective view of a first embodiment of a safety penetrating instrument according to the present invention.

FIG. 1A is an exploded perspective view of a portion of the first embodiment of the safety penetrating instrument of FIG. 1.

FIG. 2 is a cross-sectional view of the first embodiment of the invention shown in FIG. 1 taken along line 2—2 of FIG. 1.

FIG. 3 is a fragmentary side elevation view of a sleeve of expandible sponge in its expanded state suitable for use with the first embodiment of the safety penetrating instrument of FIG. 1.

FIG. 3A is a fragmentary side elevation view of an alternate embodiment of a sleeve of expandible sponge in its expanded state suitable for use with the first embodiment of the safety penetrating instrument of FIG. 1.

FIG. 4 is an exploded, broken perspective view showing an expandible sponge sleeve for attachment to a pyramid-shaped sharp, penetrating member according to the present invention.

FIG. 5 is an exploded, broken perspective view showing an expandible sponge sleeve for attachment to a conical-shaped sharp, penetrating member according to the present invention.

FIG. 5A is an exploded, broken perspective view showing another embodiment of an expandible sponge sleeve for attachment to a conical-shaped sharp, penetrating member according to the present invention.

FIGS. 6A–6D are cross-sectional views taken along line 6—6 of FIG. 3 showing the hydrated or wet state and the dry, compressed state of the expandible sponge sleeves of FIGS. 4 and 5, respectively, of the first embodiment of the safety penetrating member of FIG. 1.

FIG. 8 is a side elevation view, partly in cross-section, of another embodiment of the expandible safety penetrating member according to the present invention.

FIG. 9 is a perspective view of the supporting structure for the expandible safety penetrating member of FIG. 8.

FIG. 10 is a fragmentary perspective view of an expandible safety sleeve according to the present invention.

FIG. 15 is a perspective view of an arrangement of a plurality of expandable portions or probes and a biasing means adapted for use in the embodiment of the invention shown in FIGS. 11, 12 and 13C.

FIG. 16 is an enlarged perspective view of the expandable portions or probes of the invention depicted in FIG. 15 shown in their expanded or hydrated state.

FIG. 17 is an enlarged perspective view of an expandable portion or probe of the invention shown in its expanded or hydrated state and which is suitable for use in the embodiments of the invention of FIGS. 13A and 13D.

FIG. 18 is an enlarged perspective view of another embodiment of the safety penetrating instrument of the invention showing an arrangement of two expandable portions or probes and an optical viewing fiber extending from the distal end of a sharp, penetrating member of the safety penetrating instrument.

FIG. 28 is a perspective view showing a further embodiment of a safety penetrating instrument with a protruding sleeve made of an expandable sponge material according to the present invention.

FIG. 29 is a side elevation view in cross-section of the safety penetrating instrument of FIG. 28 showing the dry state of the protruding sleeve made of an expandable sponge material taken along line 29—29 of FIG. 28.

FIGS. 30A–30D are end views of the safety penetrating instrument of FIGS. 28 and 29 showing several embodiments of the protective protruding sleeve suitable for use with the embodiment of FIGS. 28 and 29.

FIGS. 31A and 31B are perspective views, partly in cross-section, showing additional embodiments of the protective protruding sleeve of the invention.

FIGS. 33A–33E are sequential views showing the method of use of the embodiment of the protective protruding sleeve of the safety penetrating instrument of FIGS. 28 and 29 during penetration of the instrument through an anatomical wall and into an anatomical cavity.

FIG. 37 is a perspective view showing another embodiment of the invention in the form of a safety Verres needle instrument having an expandable portion or probe shown in its extended position.

FIG. 38 is a side elevation view, partly in cross-section, taken along line 38—38 of FIG. 37, of the safety Verres needle instrument of FIG. 37 showing a biasing means for extending the expandable portion or probe .

FIGS. 39A–39C are fragmentary views of alternate embodiments of the expandable portion or probe for the safety Verres needle of FIGS. 37 and 38.

FIGS. 40 and 40A are side elevation and fragmentary views, respectively, of an alternate embodiment of the expandable portion or probe of the safety Verres needle of FIGS. 37 and 38.

FIGS. 41A–41E are sequential views showing the method of use of the embodiment of the safety Verres needle of FIGS. 37 and 38 during penetration of the needle through an anatomical wall and into an anatomical cavity and retraction of the needle from the cavity.

DESCRIPTION OF THE PREFERRED EMBODIMENTS

Figure 7A:
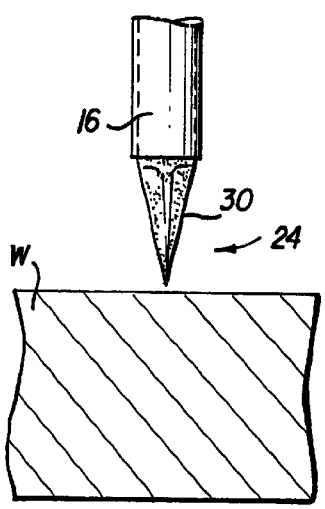
FIGS. 7A–7E are sequential views showing the method of use of the first embodiment of the safety penetrating member of FIG. 1 during penetration of the instrument through an anatomical wall and into an anatomical cavity.

The safety penetrating instrument of the present invention is described hereinafter for use as an instrument for penetrating a wall of an anatomical cavity or body lumen to form a portal for the introduction of various surgical and diagnostic instruments into the cavity during endoscopic and laparoscopic procedures. The safety penetrating instrument of the present invention may also be used for the safe penetration of any anatomical wall into an anatomical cavity or into an anatomical lumen, such as a blood vessel, for purposes of introducing fluids into or removing fluids from a cavity or lumen, such as by needles, catheters or the like. Accordingly, it is within the scope and contemplation of the present invention that the cannula or outer tubular member of the safety penetrating instrument of the invention can be a portal sleeve, trocar, needle, catheter or any tubular or luminal component of a medical instrument.

It is also contemplated within the scope of the present invention that the safety penetrating instrument of the invention can be provided with means for introducing anesthetic, antibiotic and antiseptic agents into anatomical tissues, particularly and preferably in the form of time release agents which leach out from the expandible sponge materials used in connection with the safety penetrating instrument.

Referring now to the drawings, a first embodiment of a safety penetrating instrument of the invention is shown in FIGS. 1, 1A and 2 and is designated generally by reference numeral 10. Instrument 10 includes a portal unit 12 and a penetrating unit 14. The portal unit 12 comprises a cannula in the form of an elongate sleeve 16 and a housing 18. The portal sleeve 16 is preferably a substantially cylindrical tube made of a rigid, expandable, non-expandable or flexible medically acceptable material, such as stainless steel, plastic, an expandable sponge material described hereinafter or the like, and the housing 18 may be made of the same or similar metal or plastic materials. The housing 18 preferably has a shape to facilitate grasping by a surgeon and is provided with a radially resilient seal 20 (FIG. 2) for sealingly engaging the penetrating unit 14 or any other instrument or tube passing through the housing and elongate sleeve and to close the passage in the housing and elongate sleeve when no instrument passes through the portal unit 12.

Penetrating unit 14 includes an elongate member 22, which may be hollow or solid depending on the application or procedure. In the embodiment shown, elongate member 22 is a tubular member with a distal end fitted with a sharp penetrating member 24, such as a trocar 25, and a proximal end fitted with a housing 26 which may be a fluid reservoir. The penetrating member 24 may have any suitable configuration desired for a particular procedure, such as the pyramidal trocar 25 shown in FIG. 2, a conical tip, a slanted (hypodermic needle) tip, a multifaceted tip or the like. The trocar 25 of the penetrating member 24 can be made of any suitable medical grade material, such as stainless steel or plastics and may be attached to the tubular member 22 in any conventional manner, for example, by threads, bonding, welding or the like. The trocar 25 may be hollow and preferably has at least one small passage 28 (FIG. 2) therethrough to permit fluid flow between the housing or reservoir 26 and the exterior of the penetrating tip of the trocar.

A circular plate 13, which may be a rigid metal or plastic material, a flexible or expandable material, is slidably arranged on the elongate sleeve 16 for movement therealong to a position adjacent an anatomical wall. The plate 13 preferably resiliently grips the sleeve 16 so that it can be forcibly urged to a given axial position along the sleeve and caused to remain in that position until urged to a new position. The forward surface of the plate 13 has an adhesive covering or coating and is protected by a removable or peelable sheet, paper or membrane 15 which may be removed, if desired (FIG. 1A), so that the adhesive covering of the forward surface of the plate 13 can be temporarily adhered to an anatomical wall to help support the instrument 10. A scale 17 may be inscribed or otherwise affixed to the exterior peripheral surface of the sleeve 16 adjacent the distal end thereof to facilitate determination of the depth of penetration of the instrument 10.

One or more stopcocks 19 may be connected to the sleeve 16 for insufflation or aspiration of fluids (gas or liquid) into the sleeve 16 when the elongate member 22 is removed from the sleeve.

An imaging or sensing means 21 (FIG. 1) including a viewer may be connected to the safety penetrating instrument 10 via one or more optical or sensor connections 23, 23' provided in the sleeve 16 or in the penetrating unit 14. Preferably, the connections 23, 23' include a "gooseneck" or universal joint to enable the surgeon to adjust the viewer for convenient viewing. Referring to FIG. 1A, a fiber optic or sensor output transmission line 27 may be provided longitudinally in the wall of sleeve 16 and connected to connection 23 for an optical system or physical parameter sensor. A CMOS imaging system or endoscope (not shown) may be inserted into connection 23' or through an opening 23" (FIG. 2) in the penetrating unit 14 and guided to the distal end of penetrating unit 14 to an opening 29 in the penetrating member 24 for viewing the penetrating procedure as well as imaging the operative area inside the anatomical wall and transmitting an image to an imaging apparatus similar to apparatus 21 connected to connection 23' at the proximal end of the instrument 10. A sensor probe adapted to sense parameters, such as pressure, temperature, blood chemistry, pH and the like may also be inserted into connection 23' or through an opening 23" (FIG. 2) in the penetrating unit 14 and guided to the distal end of penetrating unit 14 to an opening 29 in the penetrating member 24. A pressure sensor located in the opening 29 may be used by the surgeon to monitor the magnitude of the force applied to the penetrating instrument and to anticipate penetration by the sudden decrease in pressure magnitude accompanying passage of the sensor opening 29 through the anatomical wall.

Referring to FIGS. 4, 5 and 5A, the penetrating member 24, 24', 24" is enclosed or covered with an expandible sponge material 30, 30', 30" in the form of a sleeve or "sock" slidable on and bonded, threaded or otherwise affixed to the trocar or tip 25, 25', 25" or in the form of a coating applied to the trocar or tip. The penetrating member 24 is shown in FIG. 4 as a trocar 25 with the passage 28 exiting at one of the pyramidal faces of the trocar. In FIGS. 5 and 5A, the penetrating member 24', 24" is in the form of a conical tip 25', 25" with a passage 28', 28" exiting through the conical surface of the conical tip member 25', 25". The tip 25' may be threaded as at 25a with threads similar to self-tapping threads for securing the sock 30' to the tip 25'. As shown in FIG. 5A, the means for attaching the sock 30" may comprise recesses 25b on the conical surface of the tip 25" into which mating projections or knobs 30a engage. The tubular member 22' of the FIG. 5 embodiment has a smaller diameter than the tubular members 22, 22" of the FIGS. 4 and 5A embodiments. The passages 28, 28', 28" may be used as described above for imaging, viewing, sensing or introducing fluids into or aspirating fluids from an anatomical cavity.

A preferred expandible sponge material for the sleeves 30, 30' is a medical grade polyvinyl alcohol (PVA) sponge material, but any other expandible material may be used so long as it has the characteristics of the PVA material as described hereinafter. In the dry state, the PVA sponge material is quite hard with a hardness approximating that of wood, for example. Consequently, in the dry state, the PVA sponge sleeve 30 or coating on the penetrating member 24 has sufficient hardness so that it will not significantly inhibit penetration of the wall of an anatomical cavity. In the wet or hydrated state, the PVA sponge material is soft and compliant, and in that state, can be compressed into any desired configuration and dehydrated to maintain the compressed configuration having a relatively high hardness. Upon rehydration, the PVA sponge material becomes soft and pliant and expands to its original, uncompressed configuration. The foregoing characteristics of the PVA sponge material make it especially suitable for use in the present invention, but any compressible and expandible material having similar characteristics when hydrated and dehydrated may be used in the practice of the invention. The expandible sponge material may also incorporate anesthetic, antibiotic and antiseptic agents preferably in the form of agents which leach out, e.g., time release agents, from the expandible sponge material into anatomical tissues.

FIG. 3 illustrates the expanded or hydrated configuration of the expandible sleeves 30, 30' of FIGS. 4, 5 and 5A. As can be seen from FIGS. 1–2 and 4–5A, the expandible PVA sponge material of the sleeves 30, 30', 30" is compressed to conform to the underlying trocar 25 or conical tip 25', 25" in the dry state. When hydrated by a fluid, such as a saline solution introduced from housing 26 through passage 28, 28', 28" or by body fluids contacting the exterior surfaces of the sleeves 30, 30', 30" or both, the sleeves expand radially and longitudinally to the enlarged cylindrical configuration with a blunt or rounded end as shown in FIG. 3. FIGS. 6A and 6B illustrate in cross-section, respectively, the expanded, hydrated condition and the compressed, dry or dehydrated condition of the sleeve 30 for the trocar 25 of FIG. 4 and FIGS. 6C and 6D illustrate in cross-section, respectively, the expanded, hydrated condition and the compressed, dry or dehydrated condition of the sleeve 30', 30" for the conical tip 25', 25" of FIGS. 5 and 5A.

FIG. 3A illustrates another form of the expanded or hydrated configuration of the expandible sleeves of FIGS. 4 and 5. In this form, spines 31, which may be made of metal or plastic wire an alloy such as Nitinol or other similar material with a memory, are embedded in the dehydrated sponge material during manufacture so that upon hydration, the spines 31 help to rapidly deploy or expand the hydrated expandible material. One or more of the spines 31 may comprise an optical fiber extending to the proximal end of the instrument for viewing purposes.

Figure 7B:
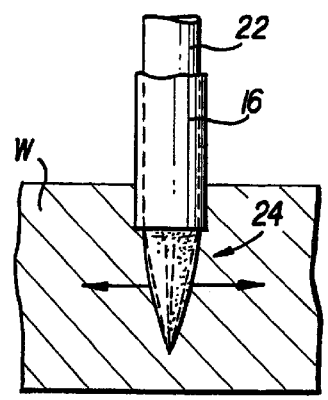
Figure 7C:
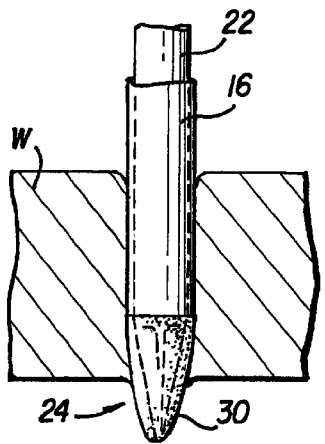
Figure 7D:
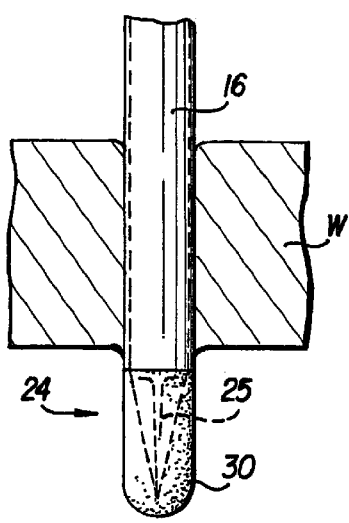
Figure 7E:
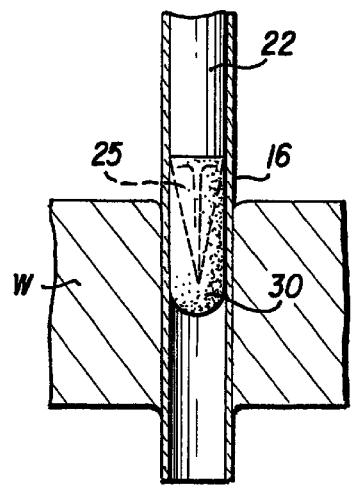

Now referring to FIGS. 7A–7E the method of using the safety penetrating instrument 10 to penetrate a wall W of an anatomical cavity will be described. It will be appreciated that the thickness of the wall W shown in the drawings relative to the dimensions of the instrument 10 may vary and may be thinner or thicker depending on the particular anatomical wall and the size of the instrument 10. Prior to penetration (FIG. 7A), the penetrating member 24 is in the form of a sharp, trocar tip covered with the hard, compressed PVA sponge sleeve 30 in its dehydrated state. In that state, the surgeon can readily apply force to the safety penetrating instrument 10 to cause the penetrating member 24 to pierce the wall W as shown in FIG. 7B. Once penetration is achieved, a fluid, such as a saline solution passing through tubular member 22 and passage 28 or body fluids in the wall W or both, begin to hydrate the sleeve 30 and cause it to expand radially as shown in FIG. 7B. During further penetration of the wall W the sleeve 30 continues to expand without significantly inhibiting the penetration capability of the instrument (FIG. 7C). When the penetrating member 24 passes completely through the wall W as shown in FIG. 7D, the sleeve is preferably fully hydrated and expanded to its soft, uncompressed state so as to protect internal organs and tissue in the anatomical cavity from damage that could result from the sharp tip of the trocar 25. When the portal sleeve 16 is in place the penetrating unit 14 is withdrawn from the portal sleeve 16 as shown in FIG. 7E and the seal 20 (FIG. 2) closes the passage in the portal sleeve. It will be understood that the expandible material, such as the PVA sponge material, may be in the form of the sleeve 30 or may be formed in situ on the trocar 25 or conical tip 25' as a coating or covering.

Referring to FIGS. 8–10, there are illustrated alternative constructions of an expandible sleeve that may be used in lieu of the sleeves 30, 30' of FIGS. 4 and 5. FIG. 8 depicts a sleeve 32 similar to sleeve 30 made of an expandible material 34, such as a PVA sponge. Sleeve 32 is provided with an internal support structure onto which the expandible material 34 may be molded comprising a coil spring 36 and a plurality of resilient longitudinal wires or spines 38 as best seen in FIG. 9. In the hydrated state of the material 34, the coil spring 36 is axially compressed and the longitudinal wires 38 are urged radially inwardly at their free ends 40 so that when the material 34 is compressed and dehydrated, the spring 36 and longitudinal wires 38 retain stored energy to assist in expanding the material 34 axially and radially, respectively, when the material is rehydrated during use. FIG. 10 illustrates another embodiment of a support structure comprising a coil spring 36' and parallel longitudinal wires 38'. In this embodiment, only axial extension of the sleeve 32' is provided by the coil spring 36'. One or more of the wires 38, 38' may comprise an optical fiber extending to the proximal end of the instrument for viewing purposes.

Figure 11:
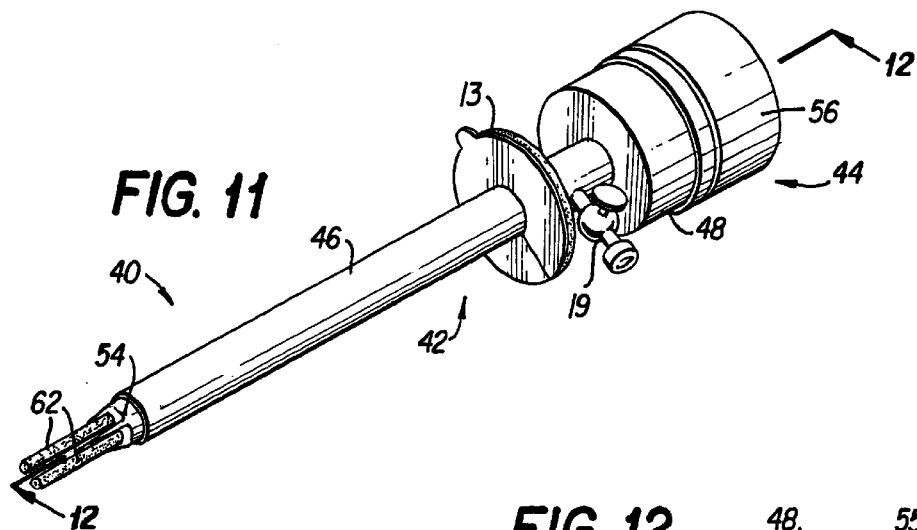
FIG. 11 is a perspective view showing another embodiment of a safety penetrating instrument according to the present invention having extendible expandable portions or probes shown in their extended positions.
Figure 12:
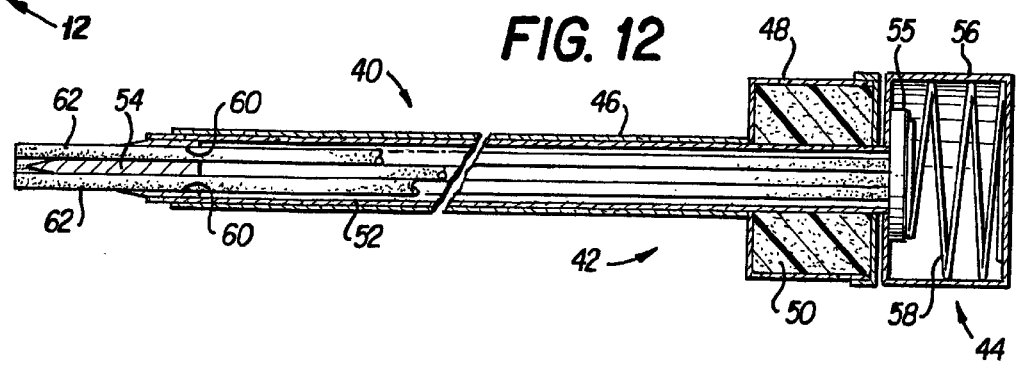
FIG. 12 is a side elevation view in cross-section of the safety penetrating instrument of FIG. 11 showing a biasing means for extending the expandable portions or probes and taken along line 12—12 in FIG. 11.

FIGS. 11 and 12 illustrate another embodiment of a safety penetrating instrument of the invention designated generally by reference numeral 40. Instrument 40 includes a portal unit 42 and a penetrating unit 44. The portal unit 42 comprises a cannula in the form of an elongate sleeve 46 and a housing 48. The portal sleeve 46 is preferably a substantially cylindrical tube made of a rigid or flexible medically acceptable material, such as stainless steel, plastic or the like, and the housing 48 may be made of the same or similar metal or plastic materials. The housing 48 preferably has a shape to facilitate grasping by a surgeon and is provided with a radially resilient seal 50 (FIG. 12) for sealingly engaging the penetrating unit 44 or any other instrument or tube passing through the housing 48 and elongate sleeve 46 and to close the passage in the housing and elongate sleeve when no instrument passes through the portal unit 42.

Penetrating unit 44 includes an elongate tubular member 52, with a distal end fitted with a sharp penetrating member, such as a trocar 54, and a proximal end fitted with a disk or plate 55 and a housing 56 which houses the disk 55 and a biasing means, such as a coil spring 58, for a purpose to be described. Housing 56 may also function as a fluid reservoir. The penetrating member 54 may have any suitable configuration desired for a particular procedure, such as the pyramidal trocar shown in FIGS. 11 and 12, a conical tip, a slanted (hypodermic needle) tip, a multifaceted tip or the like. The trocar of the penetrating member 54 can be made of any suitable medical grade material, such as stainless steel or plastics, and may be attached to the tubular member 52 in any conventional manner, for example, by threads, bonding, welding or the like. The penetrating member 54 is provided with one or a plurality of through bores 60 arranged parallel to the axis of the penetrating member 54.

Disposed in the through bore or bores 60 are one or a plurality of rods or probes 62 made, at least in part, of an expandable sponge material, such as the aforedescribed PVA sponge material, that extend from beyond the forward tip of the penetrating member 54 through the tubular member 52 to the disk 55 located in the housing 56. The rods or probes 62 may be formed entirely of the expandable sponge material with or without spines or may be formed in two or more rod sections, the forwardmost one of which is made of the expandable sponge material with or without spines and the rearwardmost one of which may be made of a medically acceptable metal or plastic material in the form of a rod or tube. As best seen in FIGS. 11 and 12, the rods or probes 62 are urged outwardly beyond the tip of the penetrating member 54 by the coil spring biasing means 58 so as to shield or shroud the sharp tip of the penetrating member 54 with the rods of expandable sponge material in their hard, dehydrated state.

As shown in FIG. 11, the instrument 40 may include the same arrangement of stopcocks 19 and slidable adhesive plate 13 depicted and described above in connection with FIGS. 1 and 2. In addition, the bores 60 may also be used as described above for CMOS imaging, viewing, sensing or introducing fluids into or aspirating fluids from an anatomical cavity.

Figure 13A:
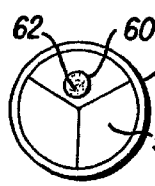
FIGS. 13A–13H are end views of the safety penetrating instrument of FIG. 11 showing various embodiments of the penetrating member and the expandable portions or probes.
Figure 13B:
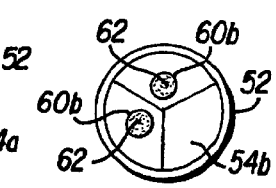
Figure 13C:
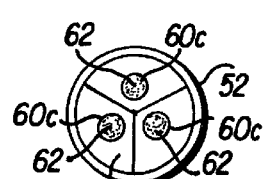
Figure 13D:
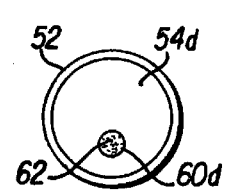
Figures 13E, 13F:
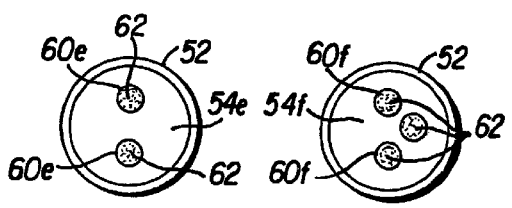
Figure 13G:
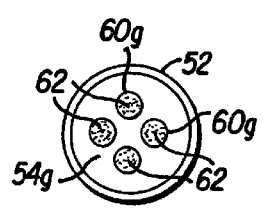
Figure 13H:
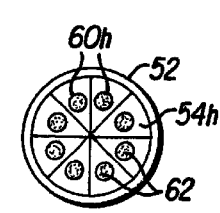

FIGS. 13A–13H illustrate various embodiments of the safety penetrating instrument 40 and its penetrating unit 44 in particular. FIGS. 13A–13C depict penetrating members 54a, 54b, 54c in the form of a trocar with one, two and three bores 60a, 60b, 60c, respectively, with rods 62 of expandable sponge material extending through the bores. FIGS. 13D–13G depict penetrating members 54d, 54e, 54f, 54g in the form of a conical tip with one, two, three and four bores 60d, 60e, 60f, 60g, respectively, with rods 62 of expandable sponge material extending through the bores. FIG. 13H depicts penetrating member 54h in the form of a multifaceted tip with eight bores 60h having rods 62 of expandable sponge material extending through the bores.

Figure 14A:
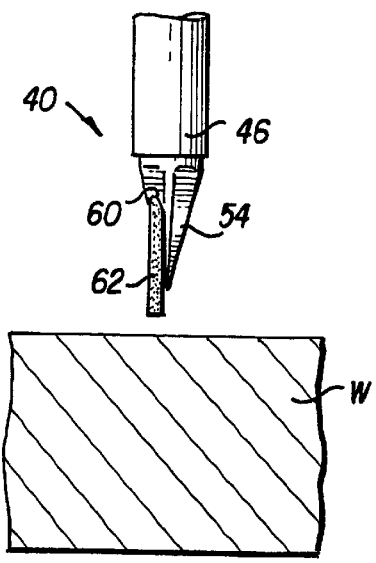
FIGS. 14A–14E are sequential views showing the method of use of the embodiment of the safety penetrating member of FIGS. 11 and 12 during penetration of the instrument through an anatomical wall and into an anatomical cavity.
Figure 14B:
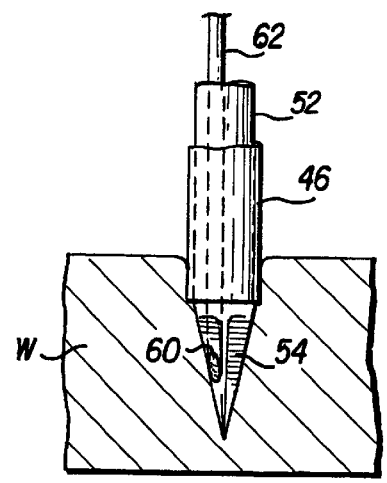
Figure 14C:
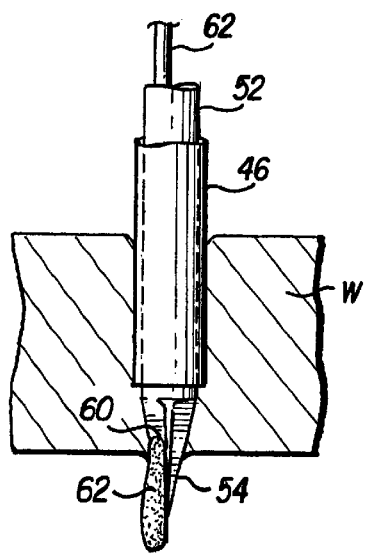
Figure 14D:
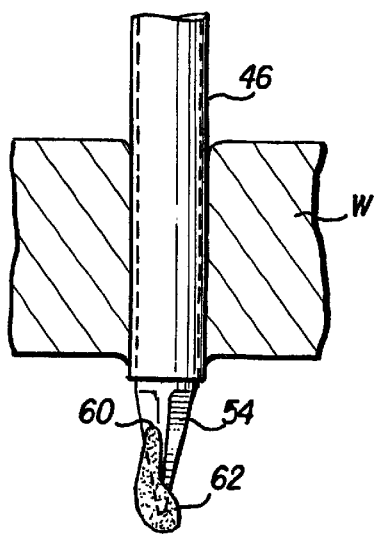
Figure 14E:
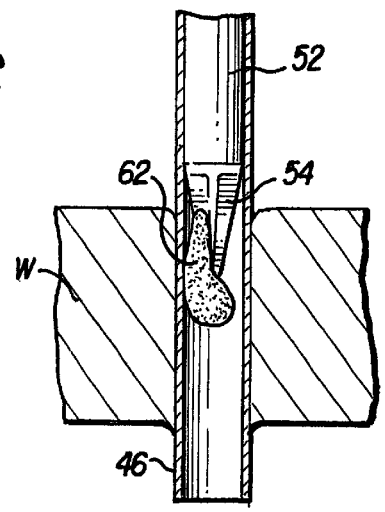

The method of use of the safety penetrating instrument 40 to penetrate a wall W of an anatomical cavity for the purpose of practicing a medical procedure, such as, for example, a laparoscopic or thorascopic procedure, is illustrated in FIGS. 14A–14E. Prior to penetration (FIG. 14A), the hard, dry expandable PVA sponge rod 62 (or rods 62 in the case of the embodiments of FIGS. 13B, 13C, etc.) extends outwardly beyond the penetrating member 54 under the axial bias or force of the coil spring 58 (FIG. 12). As the surgeon applies an axial force to the instrument 40 against the wall W, the PVA sponge rod 62 contacts the wall W and is urged rearwardly in the bore 60 against the bias of spring 58 until the sharp tip of penetrating member 54 pierces the wall W (FIG. 14B). So long as the instrument 40 is urged forwardly, the rod 62 will remain in the bore 60. Once the penetrating member 54 is in the wall W, body fluids in the wall begin to hydrate the PVA sponge rod 62. When the tip of penetrating member 54 passes through the wall W, the spring 58 urges the rod 62 outwardly as shown in FIG. 14C and the hydration of the PVA sponge by body fluids causes the rod 62 to expand also as shown in FIG. 14C. When the penetrating member 54 passes completely through the wall W as shown in FIG. 14D, the rod is preferably fully hydrated and expanded to its soft, uncompressed state so as to cover the sharp tip of the penetrating member 54 and thereby protect internal organs and tissue in the anatomical cavity from damage. When the portal sleeve 46 is in place the penetrating unit 44 is withdrawn from the portal sleeve 46 as shown in FIG. 14E and the seal 50 (FIG. 12) closes the passage in the portal sleeve.

FIG. 15 illustrates another embodiment of three rods or probes useful in the embodiment of the invention shown in FIGS. 11 and 12. In this embodiment, the rods 64 are formed in two sections, namely, a forward section 64a made of an expandable sponge, such as PVA sponge, and a rearward section 64b made of a tube, such as a stainless steel tube, connected to a disk 66 which is forwardly biased by a coil spring 68. Preferably, the rods 64a and tubes 64b are guided in parallel bores extending the length of the tubular member 52. In this embodiment of the instrument 40, the expandable PVA sponge sections 64a of the rods with or without spines are hydrated by a saline solution contained in the housing 56 which passes through the tubes 64b to the sponge sections 64a.

FIG. 16 is an enlarged view of the PVA sponge rod sections 64a of the embodiment of FIG. 15 showing the hydrated configuration of the sections 64a that would extend through the bores 60 in the penetrating member 54 (FIGS. 11 and 12). The dehydrated and hydrated PVA sponge sections may have various shapes depending on the particular procedure and degree of protection needed for internal organs or tissue. FIG. 17 illustrates an embodiment of a rod or probe 70 in which the PVA sponge section 72a is a relatively short portion of the rod 70 located at the forward end of the rod and which is guided in the bore 60 of the penetrating member 54. A rod section 72b extends through the tubular member 52 and may be a solid metal or plastic rod or a tube depending on the desired manner of hydration of the PVA sponge section 72a, i.e., whether hydration is accomplished by contact with body fluids or by a saline solution passing through the rod section 72b.

FIG. 18 depicts a further embodiment of a safety penetrating instrument 76 of the invention wherein a sharp penetrating member 78 extends through a portal sleeve 80. The penetrating member 78 is provided with a plurality of bores 82 arranged parallel to the axis of the instrument 76 through which one or more rods or probes 84 made of an expandible PVA sponge extend. In addition, a fiber optic bundle 86 extends through one of the bores 82 for viewing the anatomical cavity once the instrument has penetrated the wall of the cavity. It will be understood that one or more of the bores 82 may be used for various other purposes, such as CMOS imaging, sensing, introduction or removal of fluids, application of medication and the like.

Figure 19:
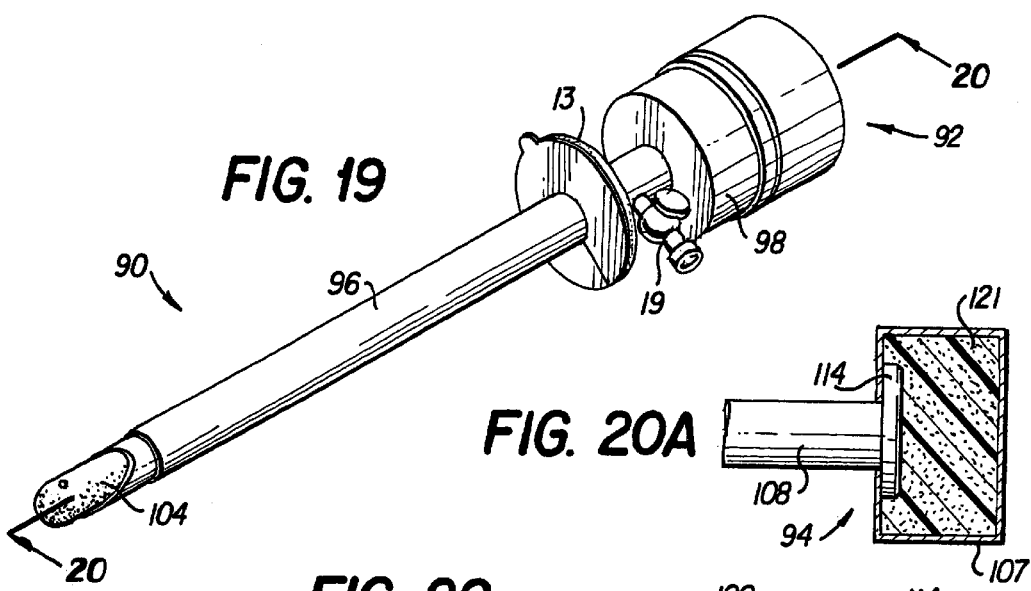
FIG. 19 is a perspective view showing another embodiment of a cannulated safety penetrating instrument according to the present invention having an expandable portion or probe shown in its extended position.
Figure 20A:
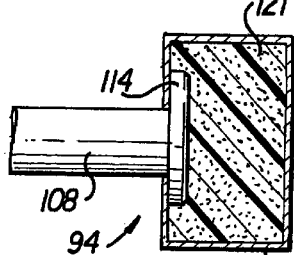
FIG. 20A is a fragmentary side elevation view showing another embodiment of the biasing means of FIG. 19.
Figure 20:
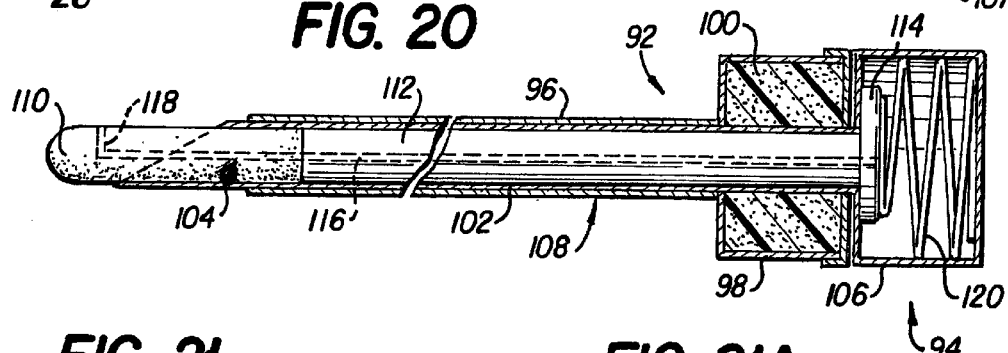
FIG. 20 is a side elevation view in cross-section of the cannulated safety penetrating instrument of FIG. 19 showing a biasing means for extending the expandable portion or probe taken along line 20—20 of FIG. 19.

Another embodiment of the safety penetrating instrument of the invention is illustrated in FIGS. 19 and 20 and is designated generally by reference numeral 90. In this embodiment, the instrument 90 comprises a portal unit 92 and a penetrating unit 94. The portal unit 92 comprises an elongate sleeve 96 and a housing 98. The portal sleeve 96 is preferably a substantially cylindrical tube made of a rigid or flexible medically acceptable material, such as stainless steel, plastic or the like, and the housing 98 may be made of the same or similar metal or plastic materials. The housing 98 preferably has a shape to facilitate grasping by a surgeon and is provided with a radially resilient seal 100 (FIG. 20) for sealingly engaging the penetrating unit 94 or any other instrument or tube passing through the housing and elongate sleeve and to close the passage in the housing and elongate sleeve when no instrument passes through the portal unit 92. As shown in FIG. 19, the instrument 90 may include the same arrangement of stopcocks 19 and slidable adhesive plate 13 depicted and described above in connection with FIGS. 1 and 2.

Penetrating unit 94 includes an elongate tubular cannula member 102, with a distal end sharpened by means of an inclined end surface to form a needle-like point 104 for penetrating the wall of an anatomical cavity, and a proximal end fitted with a housing 106 which may be a fluid reservoir as in previously described embodiments. Generally, the cannula member 102 may be characterized as a needle at diameters of about 2 mm or less and as a trocar at diameters of about 3 mm and greater. The tubular cannula member 102 can be made of any suitable medical grade material, such as stainless steel or plastics. Disposed within the tubular cannula member 102 is a cylindrical rod 108 comprising a distal end portion 110, an intermediate shaft portion 112 and a proximal end portion in the form of a disk 114. The distal end portion 110 has a rounded or blunt end and is made of an expandible sponge, preferably a PVA sponge, attached to the intermediate shaft portion 112 in any conventional manner, for example, by bonding or the like. Although the preferred expandible sponge material for the distal end portion 110 is a medical grade polyvinyl alcohol (PVA) sponge material, any other expandible material with or without spines may be used so long as it has the characteristics of the PVA material described above.

As best seen in FIGS. 19 and 20, the distal end portion 110 is urged outwardly beyond the tip of the sharpened point of the cannula by a coil spring biasing means 120 located in housing 106 so long as no rearwardly directed axial force is applied to the distal end portion. This provides an additional safety feature for the instrument 90 to prevent inadvertent "sticks" to or cuts to medical personnel.

The proximal end disk 114 is attached to the intermediate shaft portion 112 and may be formed integrally with the shaft. The cylindrical rod 108 is provided with a cental passage 116 which passes through the disk 114, shaft 112 and at least partly through the expandible PVA sponge forming the distal end portion 110. A transverse passage 118 connects the central passage 116 with the exterior of the distal end portion. As will be appreciated, a fluid, such as a saline or other aqueous solution, contained in the housing 106 may pass through the passages 116, 118 to hydrate the PVA sponge of the distal end portion 110.

FIG. 20A illustrates an alternate embodiment of the biasing means in the housing of the penetrating unit 94. In this embodiment, the housing 107 contains a resilient element 121, such as a flexible rubber or sponge material suitable for medical applications.

Figure 21:
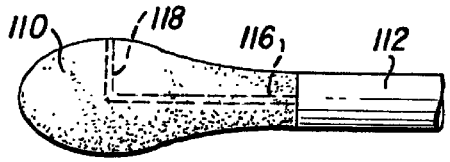
FIG. 21 is an enlarged side elevation view of the expandible portion of FIGS. 19 and 20 showing the expandable portion in its wet or hydrated state.
Figure 21A:
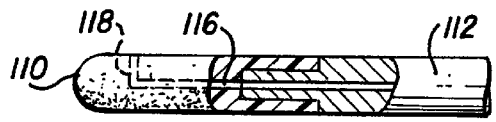
FIG. 21A is an enlarged, fragmentary side elevation view of the expandable portion of FIGS. 19 and 20 showing the expandable portion in its dry, compressed state.

FIGS. 21 and 21A depict, respectively, the expandible PVA sponge distal end portion 110 in its hydrated or wet condition and in its dry or dehydrated and compressed condition. FIG. 21A further illustrates another arrangement for attaching the PVA sponge material to the end of the intermediate shaft portion somewhat like the sleeve arrangement of FIGS. 4 and 5.

Figure 22:
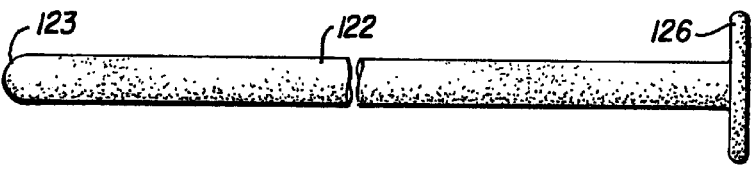
FIGS. 22 and 22A are side elevation views of two additional embodiments of the expandable portion of FIGS. 19 and 20.
Figure 22A:

FIGS. 22 and 22A show two additional embodiments of the cylindrical rod member 108 of FIGS. 19 and 20. In these embodiments, the rods 122 and 124 and disks 126 and 128 are formed entirely of an expandable sponge material and may have central and transverse passages (not shown) similar to the passages 116, 118 of the cylindrical rod 108 of the embodiment of FIGS. 19 and 20. The disks 126, 128 may also be made of a plastic material with a central hole (not shown) to permit the passage of fluid through the disks. The distal ends 123, 125 of the rods 122, 124 are rounded and inclined, respectively. The inclined distal end 125 conforms generally to the inclined needle-like point of the end of the elongate tubular cannula member 102.

Figure 23A:
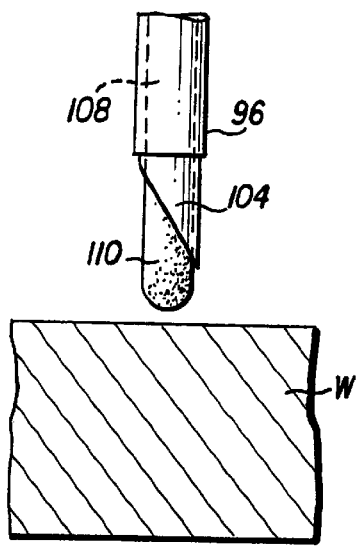
FIGS. 23A–23E are sequential views showing the method of use of the embodiment of the cannulated safety penetrating member of FIGS. 19 and 20 during penetration of the instrument through an anatomical wall and into an anatomical cavity.
Figure 23B:
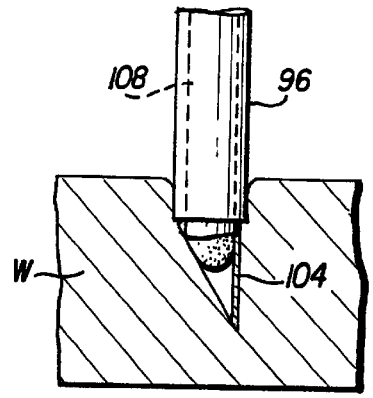
Figure 23C:
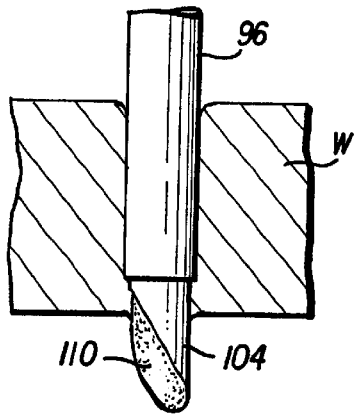
Figure 23D:
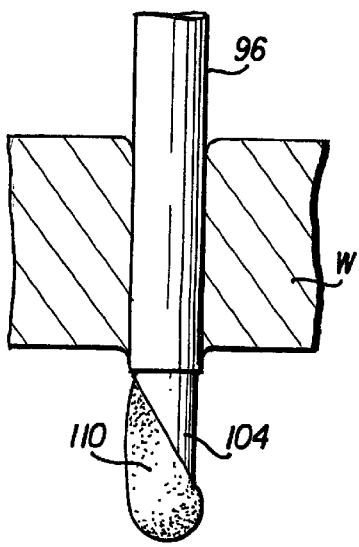
Figure 23E:
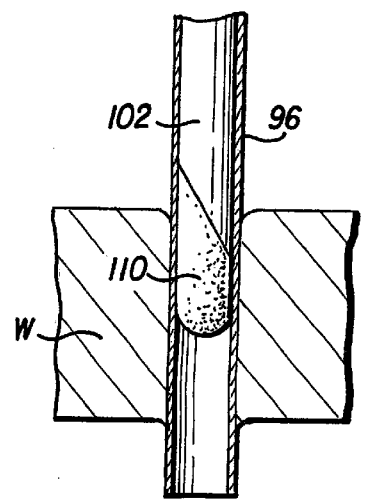

The method of use of the safety penetrating instrument 90 to penetrate a wall W of an anatomical cavity for the purpose of practicing a medical or diagnostic procedure, to introduce a fluid or medication, or to withdraw or aspirate a body fluid is illustrated in FIGS. 23A–23E. Prior to penetration (FIG. 23A), the hard, dehydrated expandable PVA sponge of the distal end portion 110 of the cylindrical rod 108 extends outwardly beyond the needle-like point 104 of the penetrating tubular cannula member 102 under the axial bias or force of the coil spring 120 (FIG. 20) or the resilient rubber or plastic spring member 121 (FIG. 20A). As the surgeon applies an axial force to the instrument 90 against the wall W, the hard PVA sponge distal end portion 110 contacts the wall W and is urged rearwardly into the tubular cannula member 102 against the bias of spring 120 or 121 until the sharp needle-like point 104 pierces the wall W (FIG. 23B). So long as the instrument 90 is urged forwardly, the cylindrical rod 108 and its distal end portion 110 will remain in the tubular cannula member 102. Once the needle-like point 104 is in the wall W, body fluids in the wall begin to hydrate the PVA sponge distal end portion 110 and, if necessary or desired, a saline or other aqueous fluid is flowed through passages 116, 118 to hydrate the PVA sponge distal end portion 110 and expand it. As the needle-like point 104 passes through the wall W, the spring 120 or 121 urges the cylindrical rod 108 outwardly as shown in FIG. 23C and the hydration of the PVA sponge by body fluids and the saline solution together with the force of spring 120 or 121 causes the expanded PVA sponge distal end portion 110 to move forwardly or outwardly from the point 104 as shown in FIG. 23C. When the needle-like point 104 passes completely through the wall W as shown in FIG. 23D, the PVA sponge distal end portion 110 is preferably fully hydrated and expanded to its soft, uncompressed state and fully extended by the spring 120 or 121 so as to cover the sharp tip of the needle-like point 104 and thereby protect internal organs and tissue in the anatomical cavity from damage. When the portal sleeve 96 is in place, the penetrating unit 94 is withdrawn from the portal sleeve 96 as shown in FIG. 23E and the seal 100 (FIG. 20) closes the passage in the portal sleeve.

Figure 24:
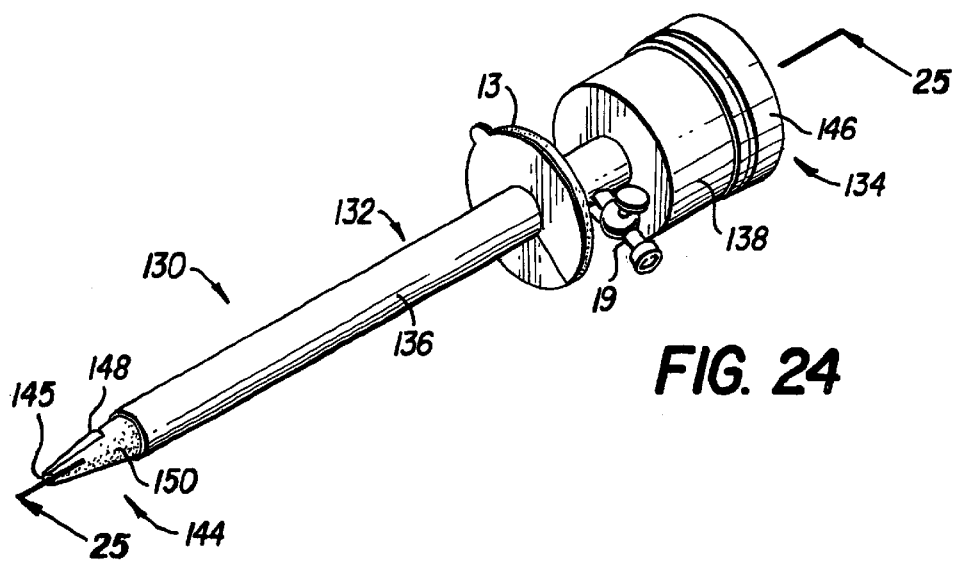
FIG. 24 is a perspective view showing another embodiment of a safety penetrating instrument with a blunt tip and bilateral blades having a coating or sleeve of an expandable sponge material according to the present invention.
Figure 25:
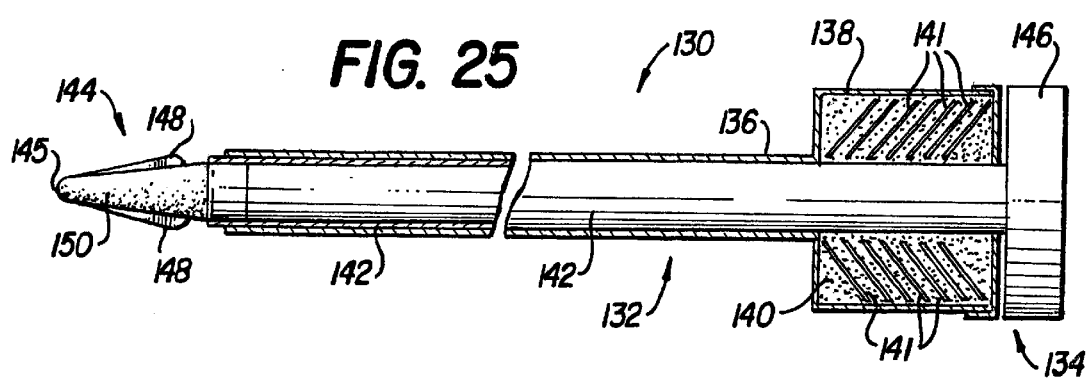
FIG. 25 is a side elevation view in cross-section of the safety penetrating instrument of FIG. 24 taken along line 25—25 of FIG. 24 showing a resilient valve means for sealing the trocar when the penetrating instrument has been removed from the trocar.

Another embodiment of the safety penetrating instrument 130 of the present invention is shown in FIGS. 24 and 25. In this embodiment, In this embodiment, the instrument 130 comprises a portal unit 132 and a penetrating unit 134. The portal unit 132 comprises an elongate portal sleeve 136 and a housing 138. The portal sleeve 136 is preferably a substantially cylindrical tube made of a medically acceptable material, such as stainless steel, plastic or the like, and the housing 138 may be made of the same or similar metal or plastic materials. The housing 138 preferably has a shape to facilitate grasping by a surgeon and is provided with a radially resilient seal 140 (FIG. 25) for sealingly engaging the penetrating unit 134 or any other instrument or tube passing through the housing and portal sleeve and to close the passage in the housing and portal sleeve when no instrument passes through the portal unit 132. The seal 140 may be made of an expandable material, such as the aforementioned PVA sponge material, having a plurality of resilient spines or leaf springs 141 molded into the sponge material for a purpose to be described hereinafter. As shown in FIG. 24, the instrument 130 may include the same arrangement of stopcocks 19 and slidable adhesive plate 13 depicted and described above in connection with FIGS. 1 and 2.

Penetrating unit 134 includes an elongate tubular member 142, with a conically shaped distal end portion 144 having a blunt tip 145 and a proximal end fitted with a housing 146 which may be a fluid reservoir. Affixed to the conical distal end 144 is a pair of knives 148 extending radially outwardly on diametrically opposite sides of the distal end. The distal end portion 144 of the penetrating unit 134 can be made of any suitable medical grade material, such as stainless steel or plastics and may be attached to the tubular member 142 in any conventional manner, for example, by threads, bonding, welding or the like. The distal end portion 144 preferably has at least one small passage (not shown) therethrough to permit fluid flow between the housing or reservoir 146 and the exterior of the conical tip of the distal end portion 144.

Figure 26:
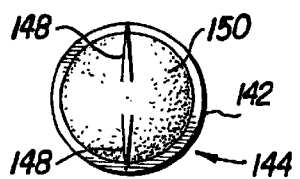
FIGS. 26 and 26A are end views of the safety penetrating instrument of FIGS. 24 and 25 showing the expandable sleeve or coating in its dry, compressed state and its wet or hydrated state, respectively.
Figure 26A:
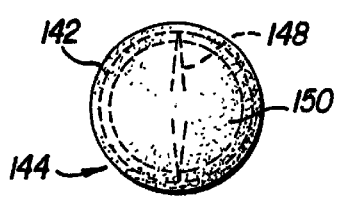
Figure 26B:
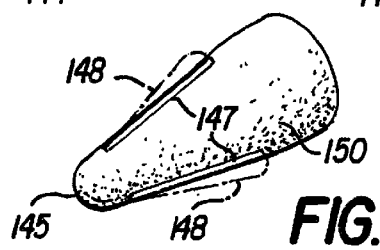
FIG. 26B is a perspective view of an expandable sleeve or sock in its dry, compressed state for use with the safety penetrating instrument of FIG. 26.

The distal end portion 144 is enclosed or covered with an expandable sponge material in the form of a sleeve or "sock" 150 slidable onto and bonded or otherwise affixed to the distal end portion 144 or in the form of an in situ coating applied to the distal end portion 144. The preferred expandible sponge material for the sleeve 150 is a medical grade polyvinyl alcohol (PVA) sponge material with the characteristics described above. When hydrated by a fluid, such as a saline solution from housing 146 or by body fluids contacting the exterior surfaces of the sleeve 150, the sleeve expands radially to cover the blades 148. FIGS. 26 and 26A illustrate end views of, respectively, the dry or dehydrated and compressed condition of the sleeve 150 and the expanded, hydrated condition of the sleeve 150 covering and enclosing the blades 148 within the PVA sponge material. FIG. 26B illustrates a perspective view of the sleeve or sock 150 provided with bilateral slots 147 into which the blades 148 extend. Other combinations and arrangements of two or more slots and blades may be used. The expandible PVA sponge material may also incorporate anesthetic, antibiotic and antiseptic agents preferably in the form of agents which leach out, e.g., time release agents, from the expandable sponge material into anatomical tissues.

The instrument 130 may also include a CMOS imaging system, viewing or sensing means or means for introducing fluids into or aspirating fluids from an anatomical cavity as described above in connection with other embodiments of the safety penetrating instrument of the invention.

Figure 27A:
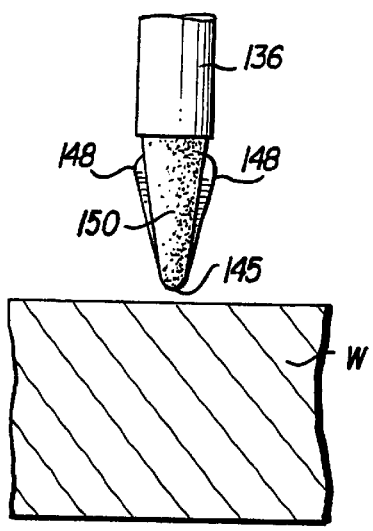
FIGS. 27A–27E are sequential views showing the method of use of the embodiment of the safety penetrating member of FIGS. 24 and 25 during penetration of the instrument through an anatomical wall and into an anatomical cavity.
Figure 27B:
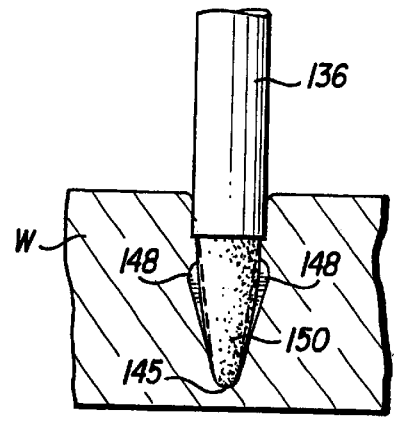
Figure 27C:
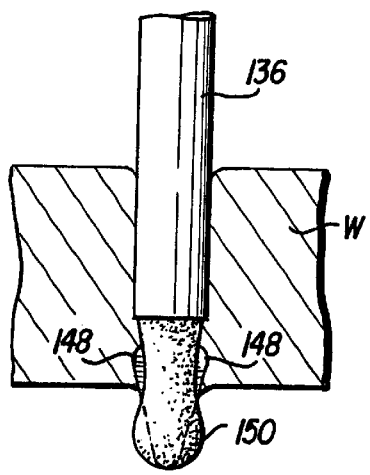
Figure 27D:
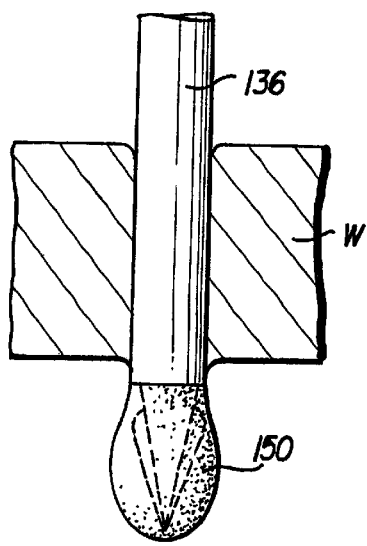
Figure 27E:
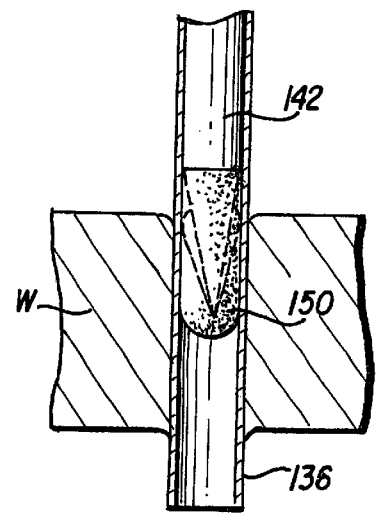

FIGS. 27A–27E illustrate the method of using the safety penetrating instrument 130 to penetrate a wall W of an anatomical cavity. Prior to penetration (FIG. 27A), the distal end portion 144 is covered with the hard, compressed PVA sponge sleeve 150 in its dehydrated state with the blades or knives 148 extending through the sleeve 150. In that state, the surgeon can readily apply force to the safety penetrating instrument 130 to cause the knives 148 to cut and penetrate the tissue of the wall W as shown in FIG. 27B. Once penetration is achieved, a fluid, such as a saline solution passing through tubular member 142 or body fluids in the wall W or both, begin to hydrate the sleeve 150 and cause it to expand radially as shown in FIG. 27B. During further penetration of the wall W the sleeve 150 continues to expand without significantly inhibiting the penetration capability of the instrument 130 (FIG. 27C). When the distal end portion 144 passes completely through the wall W as shown in FIG. 27D, the sleeve 150 is fully hydrated and expanded to its soft, uncompressed state so as to protect internal organs and tissue in the anatomical cavity from damage that could result from the knives 148 of the distal end portion 144. When the portal sleeve 136 is in place, the penetrating unit 144 is withdrawn from the portal sleeve 136 as shown in FIG. 27E and the seal 140 (FIG. 25) closes the passage in the portal sleeve. The spines or leaf springs 141 in the seal 140 are molded in place in the PVA sponge material of the seal with a set or bias such that when the seal is hydrated, the spines or springs 141 urge the softened sponge material radially inwardly to assist in closing off the passage through the seal through which the penetrating unit 144 extends.

FIGS. 28 and 29 illustrate another embodiment of a safety penetrating instrument of the present invention which is designated generally by reference numeral 152. In this embodiment, the instrument 152 comprises a portal unit 154 and a penetrating unit 156. The portal unit 154 comprises an elongate portal sleeve 158 having an integrally formed proximal end flange 160. The portal unit 154 is made of an expandable sponge material, preferably the PVA sponge material described above, which is a hard material in its dehydrated condition. In its dry condition, the flange 160 facilitates grasping by a surgeon and in its hydrated or wet condition expands radially inwardly for sealingly engaging the penetrating unit 156 or any other instrument or tube passing through the flange 160 and portal sleeve 158 and to close the central opening in the flange when no instrument passes through the portal unit 154.

The portal sleeve 158 has a coil spring 162 embedded therein adjacent the distal end thereof. In the hydrated condition of the PVA sponge material of the sleeve 158, the coil spring 162 and the PVA sponge material are axially compressed and then dehydrated to retain stored energy in the spring for later release during a medical procedure using the instrument 152. It will be appreciated that hydration of the portal sleeve 158 will release the stored spring energy and cause axial expansion or extension of the portal sleeve 158 for a purpose to be described hereinafter. It will also be understood that other spring configurations may be used to accomplish the axial extension of the portal sleeve 158.

Penetrating unit 156 includes an elongate tubular or rod member 164, with a distal penetrating end member or trocar 166 for penetrating the wall of an anatomical cavity, and a proximal end fitted with a housing 168 which may be a fluid reservoir as in previously described embodiments. The penetrating end member 166 and housing 168 can be made of any suitable medical grade material, such as stainless steel or plastics. If desired or necessary for hydration of the portal sleeve 158, one or more passages (not shown) may be provided in the elongate penetrating member 164 connecting the interior of the housing or fluid reservoir 168 with the exterior cylindrical surface of the penetrating member 164. The passages may be used as described above for imaging, viewing, sensing or introducing fluids into or aspirating fluids from an anatomical cavity.

The distal end 159 of the portal sleeve 158 is shown in its dehydrated condition in FIGS. 28 and 29 which, when hydrated without the radial support of the penetrating member 164, closes off the distal end opening of the portal sleeve. FIGS. 30A–30D illustrate four alternate embodiments of the closed configuration of the distal end 159. In those figures, the distal end closure is in the form of a pinched tube with a slit opening 170 (FIG. 30A), four flaps 172 formed by two diametrical slits 174 as openings (FIG. 30B), three flaps 176 formed by three 120° slits 178 as openings (FIG. 30C), and a rounded or conical end with a central or apex opening 180 (FIG. 30D). Other designs of the distal end opening will be apparent to those of skill in the art.

Figure 32A:
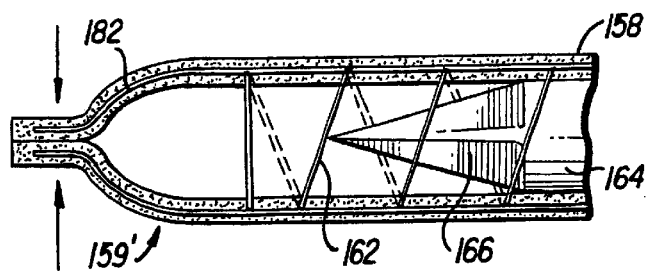
FIGS. 32A and 32B are side elevation views, in cross-section, showing operation of the embodiments of the protective protruding sleeves of FIGS. 31A and 31B to provide a protective shield for the sharp penetrating member of the safety penetrating instrument of the invention.
Figure 32B:
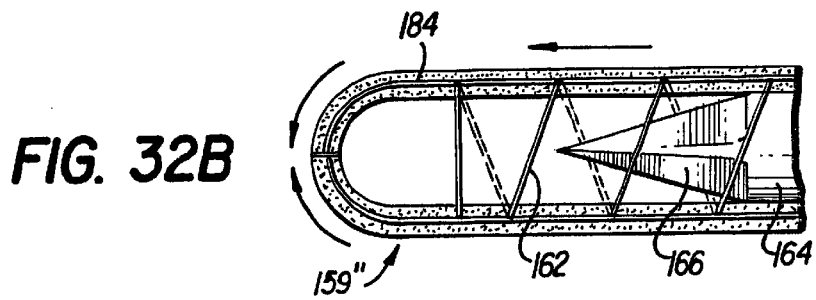

FIGS. 31A, 32A and 31B, 32B show alternate embodiments of the portal sleeve 158 in which the distal end 159' and 159" of the sleeve is provided with a plurality of longitudinal wires 182 and 184, respectively, which are biased to assist in reliably closing the distal end 159' or 159" of the sleeve 158. FIGS. 32A and 32B illustrate in cross-sectional side elevation views the manner of expansion and movement of the distal end arrangement of the safety penetrating instrument 152 of FIGS. 28 and 29 in response to the stored energy or bias of the coil spring 162 and the wires 182, 184.

FIGS. 33A–33E illustrate the method of using the safety penetrating instrument 152 of FIGS. 28–29 to penetrate a wall W of an anatomical cavity. Prior to penetration (FIG. 33A), the compressed PVA sponge portal sleeve 158 in its dehydrated state extends axially only up to the penetrating trocar point 166. In that condition, the surgeon can readily apply force to the safety penetrating instrument 152 to cause the trocar point 166 to penetrate the tissue of the wall W as shown in FIG. 33B. Once penetration is achieved, a fluid, such as a saline solution passing through passages (not shown) in penetrating tube or rod member 164 or body fluids in the wall W or both, begin to hydrate the sleeve 158 and cause it to soften (FIG. 33B). During further penetration of the wall W the sleeve 158 begins to expand axially without significantly inhibiting the penetration capability of the instrument 152 (FIG. 33C). When the distal end portion 144 passes completely through the wall W as shown in FIG. 33D, the sleeve 158 is fully hydrated and the coil spring 162 and PVA sponge material expand axially to urge the distal end 159 forwardly over the penetrating trocar 166. This, coupled with the closure of the distal end 159, completely encloses the trocar in a protective shield so as to protect internal organs and tissue in the anatomical cavity from damage that could result from the penetrating trocar point 166. When the portal sleeve 158 is in place, the penetrating unit 156 is withdrawn from the portal sleeve 158 as shown in FIG. 33E and the coil spring 162 provides the support necessary to prevent the sleeve from collapsing radially inwardly. The distal end 159 maintains an easily opened seal for the portal sleeve 158 and may serve as the only seal for the portal passage or may work in conjunction with the seal at the flange 160 to close the passage in the portal sleeve.

Figure 34:
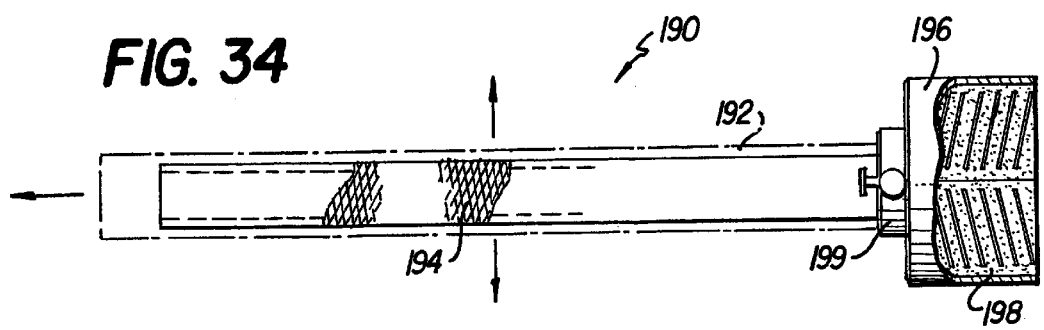
FIG. 34 is a fragmentary side elevation view of another embodiment of a safety penetrating instrument according to the present invention with a protruding sleeve made of an expandable sponge material supported by an expandable mesh material.
Figure 35A:
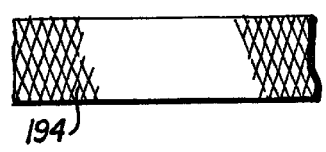
FIGS. 35A and 35B are fragmentary side elevation views showing the mesh material in the protruding and retracted conditions.
Figure 35B:
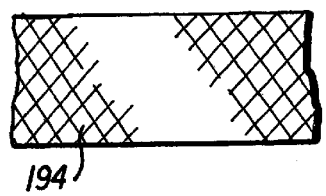
Figure 36:
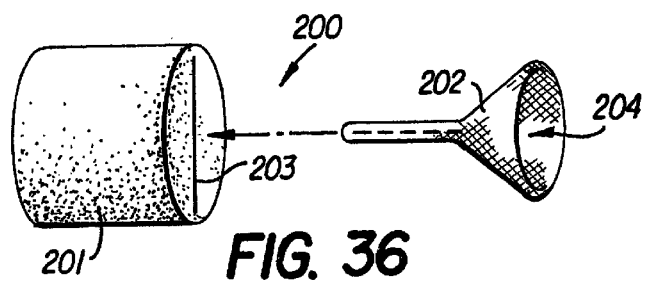
FIG. 36 is an exploded perspective view of a universal valve for sealing instruments used to penetrate the anatomical wall of an anatomical cavity.

An alternate embodiment of the safety penetrating instrument of the invention, similar to that shown in FIGS. 28 and 29, is illustrated in FIGS. 34–36 and is designated generally by reference numeral 190. In this embodiment, with reference to FIG. 34, the safety penetrating instrument 190 comprises a portal sleeve 192 made of an expandible sponge material, such as PVA sponge material, similar to the portal sleeve 158. The coil spring 162 of FIGS. 28 and 29 is replaced in this embodiment by a wire mesh tube 194 which may be axially compressed to store energy in the dehydrated condition of the portal sleeve 192 so that when the sleeve 192 is hydrated, it will expand axially to enclose and cover the sharp penetrating member (not shown) disposed in the portal sleeve. The wire mesh tube 194 may be made of a stainless steel, Nitinol® metal mesh or other medically acceptable metal or a plastic mesh material. In the case of a Nitinol® metal mesh material, the axial extension of the mesh material may be the result of stored energy alone or in combination with an increase or decrease in temperature of the mesh resulting from conduction from body tissue or from an externally applied heat or cold source, e.g., hot air, an exothermal chemical reaction or the like.

A housing 196 for a seal 198 is connected by a fitting 199 to the proximal end of the portal sleeve 192. Seal 198 may correspond to seal 140 of FIG. 25 which, in a hydrated condition, sealingly receives a suitable penetrating instrument (not shown). The housing 196 has a shape to facilitate grasping by a surgeon for urging the penetrating instrument 190 through the wall of an anatomical cavity.

In operation, after penetration of the wall of an anatomical cavity and hydration of the PVA sponge material of the portal sleeve 192, the sleeve extends axially forwardly into the anatomical cavity to enclose the sharp tip of the penetrating instrument. In the case of a stainless steel or plastic wire mesh, the diameter of the portal sleeve 192 will decrease slightly as shown by the arrows in FIG. 34 so that the inside diameter of the portal sleeve 192 in its dehydrated condition must be slightly greater than the maximum diameter of the penetrating member in the portal sleeve. This diameter reduction is shown exaggerated in FIGS. 35A and 35B. In the case of a Nitinol® metal mesh material, the axial extension of the portal sleeve 192 in response to hydration of the PVA sponge and, for example, a chemical exothermal reaction applied to the Nitinol® metal mesh, can be advantageously designed to maintain a substantially constant diameter of the portal sleeve.

FIG. 36 illustrates an exploded view of a universal seal or valve 200 comprising a resilient polymeric material body 201 which may be a sponge material, such as PVA sponge, with a metal (stainless steel mesh or Nitinol® metal mesh) or plastic mesh insert 202 in the form of a trumpet-shaped element with a converging axial passage 204. Insert 202 is positioned in the sponge body 201 via a slit 203 in the body and is designed to flex open when a penetrating member is pushed through the axial passage 204 and to flex closed when the penetrating member is removed from the passage 204. In the case of a Nitinol® metal mesh material, the opening and/or closing of the passage 204 may be assisted by application of, for example, heat to open and cold to close the passage.

Another application of the safety penetrating instrument of the invention is illustrated in FIGS. 37 and 38 in connection with a Verres needle and is designated generally by reference numeral 210. In this embodiment, the safety Verres needle instrument 210 comprises a conventional elongate Verres needle 212 with a sharp point 214 at its distal end for penetrating the wall of an anatomical cavity, and a proximal end fitted with a housing 216 containing a seal 218 (FIG. 38) and a biasing means or spring 220. The housing 216 preferably has a shape to facilitate grasping by a surgeon.

Disposed within the Verres needle 212 is a cylindrical rod 222 comprising a distal end portion 224, an intermediate shaft portion 226, a proximal end portion comprising a stopcock or valve 228 and a flange 230 disposed between the intermediate shaft portion 226 and the proximal end portion. The distal end portion 224 has a rounded or blunt end and is made of an expandible sponge, preferably a PVA sponge, attached to the intermediate shaft portion 226 in any conventional manner, for example, by bonding or the like. Although the preferred expandible sponge material for the distal end portion 224 is a medical grade PVA sponge material, any other expandible material may be used so long as it has the characteristics of the PVA material described above.

As best seen in FIG. 38, the distal end portion 224 is urged outwardly beyond the tip of the Verres needle point 214 by coil spring 220 applying an axial force to flange 230 so long as no rearwardly directed axial force is applied to the distal end portion 224. This provides an additional safety feature for the Verres needle 210 to prevent inadvertent "sticks" to or cuts to medical personnel.

The cylindrical rod 222 is provided with a cental passage 232 which passes through the intermediate shaft portion 226 and the proximal end portion and through the expandible PVA sponge forming the distal end portion 224. A transverse passage 234 connects the central passage 232 with the exterior cylindrical surface of the distal end portion 224. As will be appreciated, a fluid, such as a saline or other aqueous solution, may pass through the stopcock or valve 228 and passages 232, 234 to hydrate the PVA sponge of the distal end portion 224. Other fluids, including medications, may be introduced into an anatomical cavity through the stopcock or valve 228 and passages 232, 234 and body fluids may be aspirated from the cavity.

An imaging or sensing means 211 (FIG. 38) may be connected to the safety penetrating instrument 210 via one or more optical or sensor connections 213 provided in the sleeve 226. A CMOS imaging system may be inserted into connection 213 or through the opening in the proximal end of sleeve 226 and guided to the distal end portion 224 of the instrument for imaging the operative area inside the anatomical wall and transmitting an image or a signal from a sensor to the image or sensing means 211. A sensor probe adapted to sense parameters, such as pressure, temperature, blood chemistry, pH and the like may also be inserted into the instrument 210 and guided to the distal end portion 224.

FIGS. 39A–39C depict alternate embodiments of the shape of the expandible PVA sponge distal end portion 224 of the Verres needle instrument in its hydrated or wet uncompressed condition. FIG. 40 shows another embodiment of the cylindrical rod 222' in its dry or dehydrated and compressed condition. In this embodiment, the distal end portion 224' has a greater axial length than the distal end portion 224 of FIG. 38. The hydrated or wet expanded condition of the distal end portion 224' is illustrated in FIG. 40A. Other shapes of the distal end portion are, of course, also possible. For example, the distal end portion may be shaped similar to the needle point 214, that is, with an oblique angle generally corresponding to the oblique angle of the needle point.

The method of use of the safety Verres needle instrument 210 to penetrate a wall W of an anatomical cavity for the purpose of introducing a fluid or medication, or to withdraw or aspirate a body fluid is illustrated in FIGS. 41A–41E. Prior to penetration (FIG. 41A), the hard, dehydrated expandible PVA sponge of the distal end portion 224 of the cylindrical rod 222 extends outwardly beyond the needle-like point 214 of the Verres needle 212 under the axial bias or force of the coil spring 220 (FIG. 38). As the surgeon applies an axial force to the instrument 210 against the wall W, the hard PVA sponge distal end portion 224 contacts the wall W and is urged rearwardly into the Verres needle 212 against the bias of spring 220 until the sharp needlelike point 214 pierces the wall W (FIG. 41B). So long as the instrument 210 is urged forwardly, the cylindrical rod 222 and its distal end portion 224 will remain in the Verres needle 212. Once the needle-like point 214 is in the wall W, body fluids in the wall begin to hydrate the PVA sponge distal end portion 224 and, if necessary or desired, a saline or other aqueous fluid is flowed through passages 232, 234 to hydrate the PVA sponge distal end portion 224. When the needle-like point 214 passes through the wall W, the spring 220 urges the cylindrical rod 222 outwardly as shown in FIG. 41 C and the continued hydration of the PVA sponge by body fluids and the saline solution causes the PVA sponge distal end portion 224 to expand also as shown in FIG. 41C. When the needle-like point 214 passes completely through the wall W as shown in FIG. 41D, the PVA sponge distal end portion 224 is preferably fully hydrated and expanded to its soft, uncompressed state and fully extended by the spring 220 so as to cover the sharp tip of the needle-like point 214 of the Verres needle and thereby protect internal organs and tissue in the anatomical cavity from damage. In the condition of FIG. 41D, fluids (gaseous or liquid), medications and the like may be introduced into the anatomical cavity through the passages 232, 234 and body fluids may be aspirated from the cavity. After completion of the medical procedure or procedures using the Verres needle, the instrument 210 is withdrawn from the anatomical wall W as shown in FIG. 41E.

Figure 42:
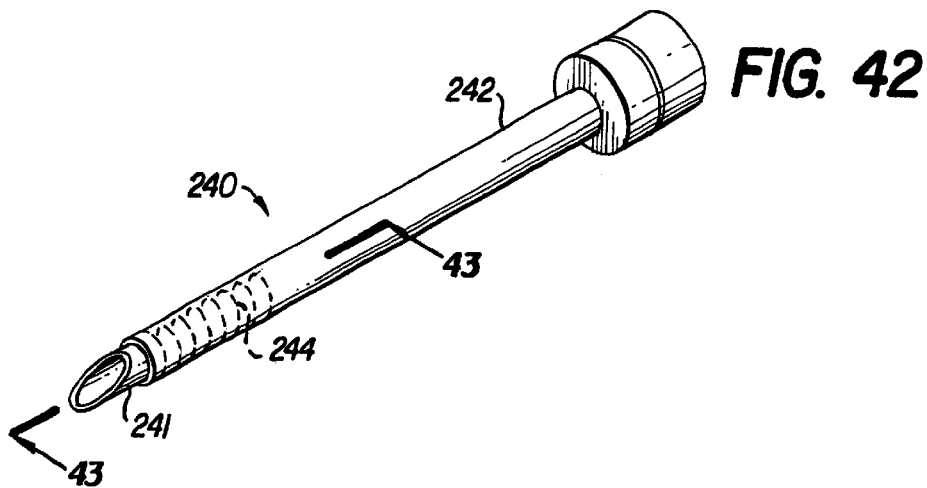
FIG. 42 is a perspective view showing a further embodiment of a safety vascular needle instrument with a protruding sleeve made of an expandible sponge material according to the present invention.
Figure 43:
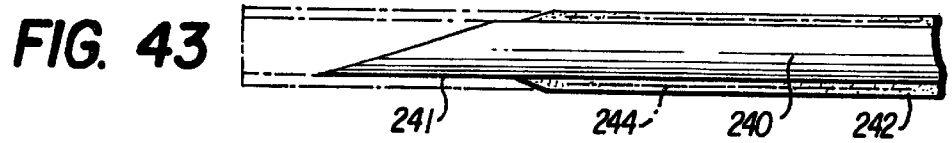
FIG. 43 is a fragmentary side elevation view in cross-section taken along line 43—43 of the safety vascular needle instrument of FIG. 42.

Another embodiment of the present invention is illustrated in FIGS. 42 and 43 and comprises a safety intravascular needle 240 having a sharp point 241 and a sleeve or covering 242 made of an expandible sponge material, such as the above described PVA sponge material. Preferably, the sleeve 242 has molded therein an axially compressed coil spring 244 in a manner similar to the embodiment of the invention shown in FIGS. 28 and 29. In the embodiment of FIGS. 42 and 43, the PVA sponge material of the sleeve 242 is compressed with the spring 244 and dehydrated such that the sharp point 241 of the needle 240 extends axially beyond the sleeve 242.

Figure 44A:
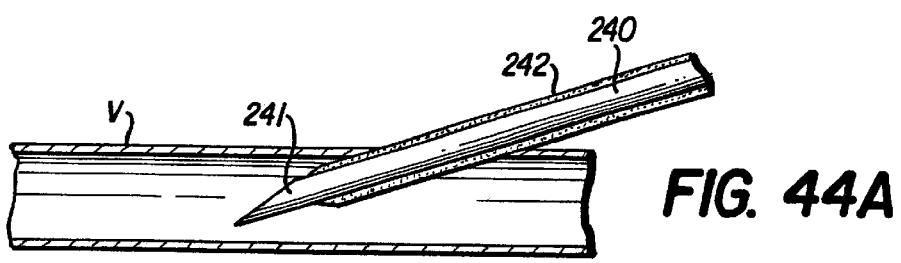
FIGS. 44A and 44B are fragmentary side elevation views, in cross-section, showing the operation of the protruding expandible sponge sleeve for the safety vascular needle instrument of FIGS. 42 and 43.
Figure 44B:
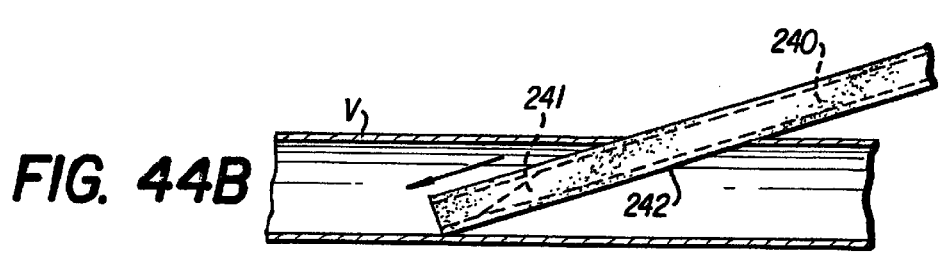

When the needle 240 is used to penetrate a blood vessel V (FIG. 44A), sleeve 242 is hydrated by blood in the vessel and the PVA sponge material of the sleeve 242 and the spring 244 extend axially beyond the sharp point 241 to protect the walls of the vessel from damage by the point 241 (FIG. 44B). It is also possible to remove the needle 240 from the sleeve 242 and leave the sleeve in place in the blood vessel V for purposes of infusing intravenous fluids. Other needle configurations may be used, such as a Tuohy needle.

Figure 45:
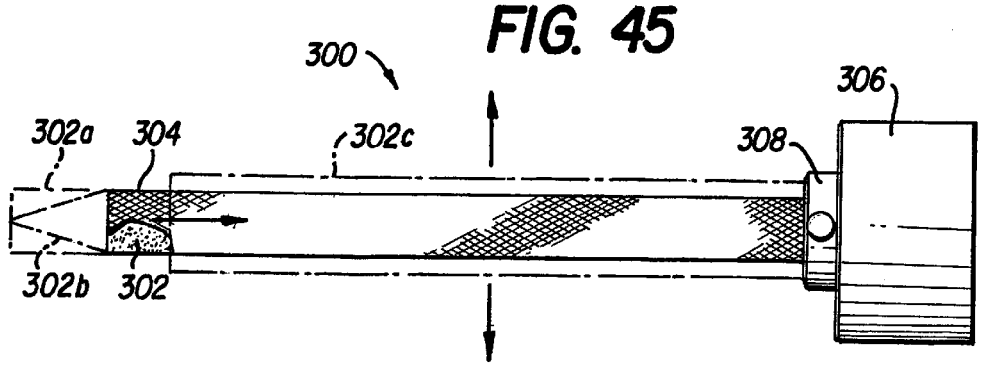
FIG. 45 is a side elevation view of another embodiment of a safety penetrating instrument according to the present invention with a protruding sleeve made of an expandible sponge material supported by an expandible mesh material.
Figure 45A:
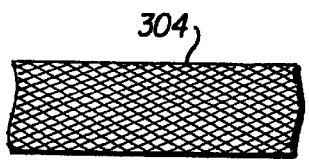
FIGS. 45A and 45B are fragmentary side elevation views showing the mesh material in the protruding and retracted conditions.
Figure 45B:
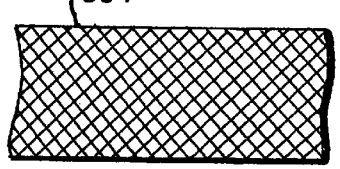

Now referring to FIGS. 45, 45A and 45B there is shown another embodiment of the invention which is designated generally by reference numeral 300. In this embodiment, with reference to FIG. 45, the safety penetrating instrument 300 comprises a portal sleeve 302 made of an expandible sponge material, such as PVA sponge material, similar to the portal sleeve 192 of FIG. 34. In this embodiment, a wire mesh tube 304 is molded with the expandible material of sleeve 302 and is axially stretched to store energy in the dehydrated condition of the portal sleeve 302 so that when the sleeve 302 is hydrated, it will contract axially and expand radially to enlarge the bore in which a safety penetrating instrument or other instrument (not shown) is disposed. A further distal end extension 302a, 302b of the sleeve 302 without the wire mesh embedded therein may be provided at the distal end of the sleeve 302 to cover the sharp penetrating member (not shown) disposed in the portal sleeve. The extension 302a or 302b may be axially compressed in the dehydrated state so that when hydrated it will extend axially and radially while the remaining portion of the sleeve 302 is contracting axially and expanding radially. The wire mesh tube 304 may be made of a stainless steel, Nitinol® metal mesh or other medically acceptable metal or a plastic mesh material. In the case of a Nitinol® metal mesh material, the axial contraction of the mesh material may be the result of stored energy alone or in combination with an increase or decrease in temperature of the mesh resulting from conduction from body tissue or from an externally applied heat or cold source, e.g., hot air, an exothermal chemical reaction or the like. The distal end extension 302b may be formed in its dehydrated state as a sharp point for a penetrating instrument. It will be appreciated by those skilled in the art that various combinations of compression and extension or stretching of the expandible material of the invention are possible to achieve a particular medical objective, such as enlarging the diameter of a sleeve to accommodate larger diameter instruments, extending, expanding or contracting a sleeve or probe radially and/or axially to protect tissue or organs from damage by a sharp point, or for other purposes.

A housing 306 for a seal (not shown) is connected by a fitting 308 to the proximal end of the portal sleeve 3022. The seal 198 may correspond to seal 140 of FIG. 25 which, in a hydrated condition, sealingly receives a suitable penetrating instrument (not shown). The housing 306 has a shape to facilitate grasping by a surgeon for urging the penetrating instrument through the wall of an anatomical cavity.

In operation, after penetration of the wall of an anatomical cavity and hydration of the PVA sponge material of the portal sleeve 302, the sleeve contracts axially rearwardly into the larger diameter configuration 302c and the distal end extension 302a or 302b extends axially into the anatomical cavity to enclose the sharp tip of the penetrating instrument. This diameter increase of sleeve portion 302c is shown exaggerated in FIGS. 45A and 45B.

Figure 46:
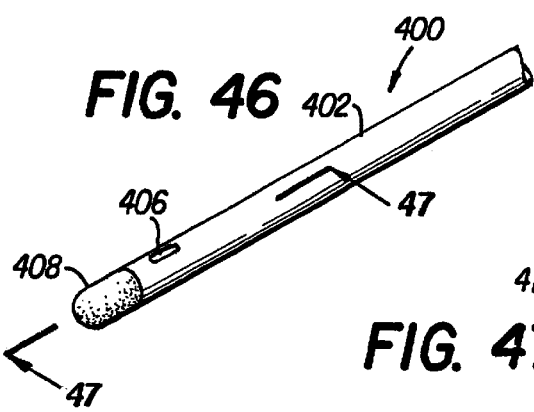
FIG. 46 is a perspective view showing a further embodiment of a safety catheter instrument with a penetrating tip made of an expandible sponge material according to the present invention.
Figure 47:
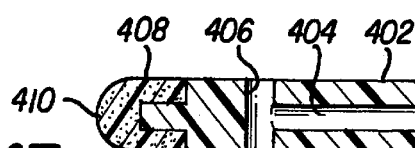
FIG. 47 is a fragmentary side elevation view in cross-section taken along line 47—47 of the safety catheter instrument of FIG. 46.
Figure 47A:
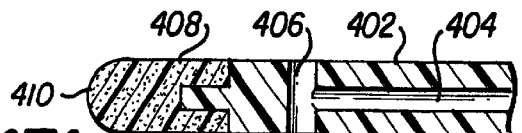
FIG. 47A is a fragmentary side elevation view in cross-section of the safety catheter instrument of FIGS. 46 and 47 showing the expanded condition of the catheter tip.

Another embodiment of the present invention is illustrated in FIGS. 46, 47 and 47A and comprises a safety catheter instrument 400 comprising a catheter 402 which may be a flexible, semirigid or rigid tubular member having a central passage 404 interconnected with a transverse passage 406. The catheter 400 is provided with a blunt tip 408 comprising a sleeve or covering 410 made of an expandible sponge material, such as the above described PVA sponge material. In its dehydrated condition shown in FIG. 47, the expandible sponge material of the sleeve 410 is axially compressed to provide sufficient stiffness for initial penetration, for example, into the urethra. Upon penetration, hydration of the sleeve 410 by body fluids in the urethra or by an added lubricant, for example, causes the sleeve to expand axially as shown in FIG. 47A and become substantially softer so that passage of the catheter through the urethra is more comfortable. The sleeve 410 may also have incorporated therein a local anesthetic agent that is released upon hydration of the sleeve. Other types of blunt penetrating instruments, including trocars, needles, catheters and the like, may also be provided according to the invention with a safety penetrating tip comprising a sleeve or covering made of an expandible sponge material.

It will be understood by those skilled in the art to which this invention pertains that, while a number of the embodiments illustrate the safety penetrating instrument penetrating the anatomical wall perpendicularly, the instrument may be used at any suitable oblique angle with respect to the wall. In addition, the thickness of the anatomical wall W shown in the drawings is for illustrative purposes only and those skilled in the art will appreciate that the safety penetrating instrument of the present invention may be used to penetrate anatomical walls of different thicknesses, e.g., the skin and wall of a blood vessel or other body lumen, the wall of the abdominal cavity, etc.

It will also be understood that the various features of a particular embodiment may be used with other embodiments even though such feature or features may not be specifically illustrated or described in connection with those other embodiments. For example, without limitation, the forming of the expandible sponge material with or without spines is contemplated for all embodiments where such spines are useful, the incorporation of imaging (CMOS, CCD or other), viewing, and sensing systems in each embodiment where it is desirable, the application of medicaments and other agents by way of passages or incorporation in the expandible sponge material, and the incorporation of the described stopcocks and/or movable adhesive plates are all contemplated within the scope of the present invention.

Although certain presently preferred embodiments of the present invention have been specifically described herein, it will be apparent to those skilled in the art to which the invention pertains that many variations and modifications of the various embodiments shown and described herein may be made without departing from the spirit and scope of the invention. Accordingly, it is intended that the invention be limited only to the extent required by the appended claims and the applicable rules of law.

What I claim is:

1. A safety penetrating instrument with proximal and distal ends for penetrating a wall of an anatomical cavity or lumen, comprising an elongated penetrating member having a distal end and a proximal end, the distal end of said elongated member comprising a tip including a sharp element for piercing the wall of the anatomical cavity, an outermost covering adhering over said sharp element said covering comprising a material having a first state with a first hardness and a second state with a second hardness less than the first hardness, whereby, when the distal end of the elongated member passes from a position outside the cavity or lumen to a position inside the cavity or lumen, at least a portion of said covering transitions from the first state to the second state to form a protective member for said sharp element of the tip.

2. The safety penetrating instrument of claim 1, wherein said covering material is an expandible sponge material.

3. The safety penetrating instrument of claim 1, wherein said covering material is a polyvinyl alcohol sponge material.

4. The safety penetrating instrument of claim 1, wherein said covering material in its first hardness state is hydrated to cause it to transition from its first hardness state to its second hardness state.

5. The safety penetrating instrument of claim 1, wherein said covering comprises one of a sock, sleeve or coating on said at least a portion of said tip.

6. The safety penetrating instrument of claim 1, wherein said covering has at least one of an anesthetic, antibiotic or antiseptic agent incorporated therein.

7. The safety penetrating instrument of claim 1, including at least one spine in said covering.

8. The safety penetrating instrument of claim 1, including a portal sleeve for slidably receiving said elongated penetrating member, means connected to said portal sleeve for insufflating a fluid into or aspirating a fluid from said portal sleeve.

9. The safety penetrating instrument of claim 8, including a plate mounted on said portal sleeve, said plate having front and back surfaces and an adhesive layer on said front surface.

10. The safety penetrating instrument of claim 9, wherein said plate is axially movable along said portal sleeve.

11. The safety penetrating instrument of claim 1, wherein the penetrating member is one of a trocar, cannula, needle, intravenous needle, Verres needle, Tuohy needle, catheter.

12. The safety penetrating instrument of claim 1, wherein said covering is attached to said tip by one of bonding, threading and mating recesses and projections.

13. A safety penetrating instrument for penetrating an anatomical wall or body lumen, comprising a portal sleeve having proximal and distal ends, an elongated penetrating member axially movable in said portal sleeve and having a distal end and a proximal end, the distal end of said elongated penetrating member comprising a tip including a sharp element for piercing the anatomical wall, an outermost covering adhering over said sharp element, said covering comprising a material having a first state with a first hardness and a second state with a second hardness less than the first hardness, and means connected to said elongated penetrating member for causing said covering material to transition from said first hardness state to said second hardness state, whereby, when the distal end of the elongated penetrating member passes from a position outside the anatomical wall to a position inside the anatomical wall, at least a portion of said covering transitions from the first state to the second state to form a protective member for said sharp element of the tip.

14. The safety penetrating instrument of claim 13, wherein said covering material is an expandible sponge material, said means for causing said covering material to transition from said first hardness state to said second hardness state comprising means for hydrating the expandible sponge material when said elongated penetrating member penetrates the anatomical wall.

15. The safety penetrating instrument of claim 13, including a housing connected to the proximal end of the portal sleeve, said housing being adapted to contain a fluid for hydrating the expandible sponge material.

16. The safety penetrating instrument of claim 13, wherein said penetrating member is one of a trocar, cannula, needle, intravenous needle, Verres needle, Tuohy needle, catheter.

17. The safety penetrating instrument of claim 13, including means connected to said portal sleeve for insufflating a fluid into or aspirating a fluid from said portal sleeve, a plate mounted for axial movement on said portal sleeve, said plate having front and back surfaces and an adhesive layer on said front surface and a removable sheet on said adhesive layer.

18. The safety penetrating instrument of claim 13, wherein said covering comprises a disposable sock or sleeve attachable to and detachable from said tip.

19. The safety penetrating instrument of claim 13, including a scale on the portal sleeve.

20. A safety penetrating instrument with proximal and distal ends for penetrating a wall of an anatomical cavity or for penetrating a body lumen, comprising an elongated penetrating member having a distal end and a proximal end, the distal end of said elongated member having a tip for piercing the wall of the anatomical cavity or for penetrating the body lumen, a covering adhering to at least a portion of said tip, said covering comprising a material having a first state with a first hardness and a second state with a second hardness less than the first hardness, whereby, when the distal end of the elongated member passes from a position outside the cavity or lumen to a position inside the cavity or lumen, at least a portion of said covering transitions from the first state to the second state to form a protective member for said tip.

21. A method of penetrating an anatomical wall using an elongated penetrating member having a distal end and a proximal end, the distal end of said elongated penetrating member having a tip with a sharp element for piercing the anatomical wall, an outermost covering for said sharp element, said covering comprising a material having a first state with a first hardness and a second state with a second hardness less than the first hardness, comprising the steps of:

with the covering in the first state placing the covering directly against the anatomical wall; and urging the covering and the sharp element into the anatomical wall to penetrate the wall whereby, during penetration at least a portion of said covering transitions from the first state to the second state to form a protective member for the sharp element of the tip.

22. The method of claim 21, wherein said covering is an expandible sponge material and including the step of hydrating the covering to cause the transition from the first state to the second state.

23. A safety penetrating instrument for penetrating a wall of an anatomical cavity or lumen, comprising:

an elongated penetrating member having a distal end and a proximal end, the distal end having a leading end section and being sized and adapted for entering into the wall of the anatomical cavity or lumen; and an expandible member comprising an outermost covering over a sharp tip of the leading end section and fabricated from an expandible material having a dry, compacted, hard state before entering into the wall of the anatomical cavity or lumen and a wet, soft, expanded state after entering into the wall of the anatomical cavity or lumen, whereby, when the distal end passes from a position outside the anatomical cavity or lumen to a position inside the anatomical cavity or lumen, at least a portion of the expandible member adjacent the distal end is hydrated causing the expandible member to expand from the dry, hard, compacted state to the wet, soft, expanded state forming a protective barrier over at least the leading end section of the distal end.

24. A safety penetrating instrument according to claim 23, wherein the leading end section is one of a sharp tip and a blunt tip.

* * * * *